US011406629B2

(12) United States Patent
Stahly et al.

(10) Patent No.: US 11,406,629 B2
(45) Date of Patent: *Aug. 9, 2022

(54) SOLID FORMS COMPRISING 4-AMINO-2-(2,6-DIOXOPIPERIDINE-3-YL) ISOINDOLINE-1,3-DIONE AND A COFORMER, COMPOSITIONS AND METHODS OF USE THEREOF

(71) Applicant: Celgene Corporation, Summit, NJ (US)

(72) Inventors: G. Patrick Stahly, West Lafayette, IN (US); David Jonaitis, Brookston, IN (US); Ho-Wah Hui, Basking Ridge, NJ (US); Kevin J. Klopfer, Flemington, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/061,456

(22) Filed: Oct. 1, 2020

(65) Prior Publication Data

US 2021/0100785 A1     Apr. 8, 2021

Related U.S. Application Data

(60) Continuation of application No. 16/459,435, filed on Jul. 1, 2019, now Pat. No. 10,835,522, which is a continuation of application No. 15/917,421, filed on Mar. 9, 2018, now Pat. No. 10,376,503, which is a continuation of application No. 15/607,163, filed on May 26, 2017, now Pat. No. 9,974,780, which is a division of application No. 14/780,289, filed as application No. PCT/US2014/031694 on Mar. 25, 2014, now Pat. No. 9,695,146.

(60) Provisional application No. 61/805,444, filed on Mar. 26, 2013.

(51) Int. Cl.
| A61K 31/454 | (2006.01) |
| C07D 401/04 | (2006.01) |
| C07C 55/08  | (2006.01) |
| C07C 65/03  | (2006.01) |
| C07C 65/21  | (2006.01) |
| C07C 69/88  | (2006.01) |
| C07C 305/04 | (2006.01) |
| C07C 307/02 | (2006.01) |
| C07D 275/06 | (2006.01) |
| C07D 309/40 | (2006.01) |
| C07H 3/02   | (2006.01) |
| A61K 47/02  | (2006.01) |
| A61K 47/12  | (2006.01) |
| C07D 419/14 | (2006.01) |
| G01N 23/2005 | (2018.01) |

(52) U.S. Cl.
CPC ............ *A61K 31/454* (2013.01); *A61K 47/02* (2013.01); *A61K 47/12* (2013.01); *C07C 55/08* (2013.01); *C07C 65/03* (2013.01); *C07C 65/21* (2013.01); *C07C 69/88* (2013.01); *C07C 305/04* (2013.01); *C07C 307/02* (2013.01); *C07D 275/06* (2013.01); *C07D 309/40* (2013.01); *C07D 401/04* (2013.01); *C07D 419/14* (2013.01); *C07H 3/02* (2013.01); *G01N 23/2005* (2013.01); *C07B 2200/13* (2013.01); *C07C 2601/14* (2017.05)

(58) Field of Classification Search
CPC .................................................. A61K 31/454
See application file for complete search history.

(56) References Cited

U.S. PATENT DOCUMENTS

| 5,635,517 A | 6/1997 | Muller et al. |
| 6,316,471 B1 | 11/2001 | Muller et al. |
| 7,709,031 B2 | 5/2010 | Greenway et al. |
| 2008/0051431 A1 | 2/2008 | Verhelle et al. |

FOREIGN PATENT DOCUMENTS

| WO | 2011/050962 A1 | 5/2011 | |
| WO | 2013012485 A2 | 1/2013 | |
| WO | WO-2014160690 A1 * | 10/2014 | ............... C07H 3/02 |

OTHER PUBLICATIONS

Lacy "Pomalidomide (CC4047) Plus Low-Dose Dexamethasone as Therapy for Relapsed Multiple Myeloma" J Clin Oncol 2009, 27:5008-5014.*
Steed, "The role of co-crystals in pharmaceutical design," Trends in Pharmacological Sciences, 34(3):185-193 (2013).
Banker et al., 37 Modern Pharmaceutics, 3rd edition, Marcel Dekker, New York, pp. 451 and 596 (1996).
Beaumont et al., "Design of ester prodrugs to enhance oral absorption of poorly permeable compounds: challenges to the discovery scientist," Current Drug Metabolism, 4:461-485 (2003).
Celgene assigned patents/applications indexed with pomalidomide from USPATFULL accessed Oct. 27, 2016.
Choi et al., "Role of gallic acid in inflammatory allergic process," Korean Journal of Physiology & Pharmacology, 10(2):101-108 (2006). Abstract only.
Kumar et al., "Thalidomide and lenalidomide in the treatment of multiple myeloma," Eur J. Cancer, 42(11):1612-1622 (2006).
Online "http://www.accessdata.fda.gov/drugsatfda_docs/nda/2013/204026Orig1s000PharmR.pdf" dated to Dec. 13, 2012 by Google, accessed Oct. 29, 2016.
Peterson et al., "Expanding the scope of crystal form evaluation in pharmaceutical science," J. Pharm. Pharmaceut. Sci., 9(3):317-326 (2006).

(Continued)

*Primary Examiner* — David K O'Dell
(74) *Attorney, Agent, or Firm* — Jones Day

(57) ABSTRACT

Provided herein are solid forms comprising (a) 4-amino-2-(2,6-dioxopiperidine-3-yl)isoindoline-1,3-dione and (b) a coformer. Pharmaceutical compositions comprising the solid forms (e.g., cocrystals) and methods for treating, preventing and managing various disorders are also disclosed.

27 Claims, 14 Drawing Sheets

(56) References Cited

OTHER PUBLICATIONS

Figure 1:
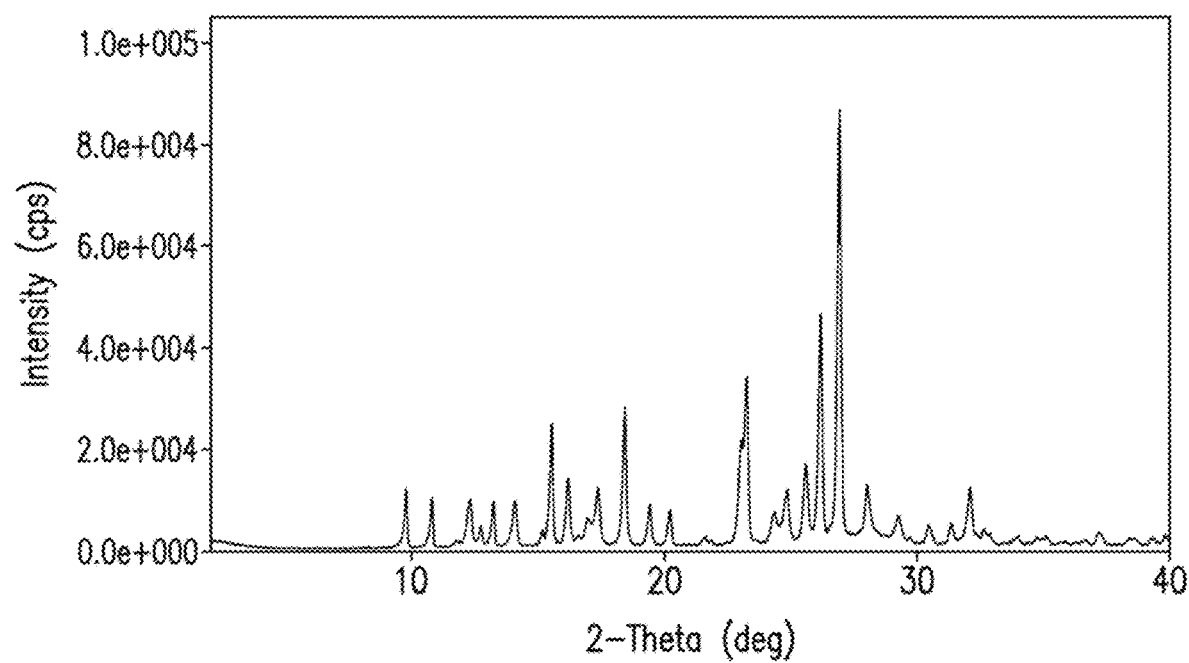

Rautio et al., "Prodrugs: design and clinical applications," Nature Reviews Drug Discovery, 7:255-270 (2008).
Verma et al., "Gallic acid: molecular rival of cancer," Environ. Toxicol. Phramacol., 35(3):473-485 (2013).
Wolff, Manfred E., "Burger's Medicinal Chemistry, 5th edition, Part 1," John Wiley & Sons, pp. 975-977 (1995).
Chanan-Khan, "Pomalidomide: the new immunomodulatory agent for the treatment of multiple myeloma," Blood Cancer J., 3:e143 (2013).

* cited by examiner

US 11,406,629 B2

SOLID FORMS COMPRISING 4-AMINO-2-(2,6-DIOXOPIPERIDINE-3-YL) ISOINDOLINE-1,3-DIONE AND A COFORMER, COMPOSITIONS AND METHODS OF USE THEREOF

This application is a Continuation of U.S. application Ser. No. 16/459,435, filed Jul. 1, 2019, which is a Continuation of U.S. application Ser. No. 15/917,421, filed Mar. 9, 2018, which is a Continuation of U.S. application Ser. No. 15/607,163, filed May 26, 2017, which is a Divisional of U.S. application Ser. No. 14/780,289, filed Sep. 25, 2015, now U.S. Pat. No. 9,695,146, which is a national phase entry pursuant to 35 U.S.C. § 371 of International Application No. PCT/US2014/031694, filed Mar. 25, 2014, which claims priority to U.S. Provisional Application No. 61/805,444, filed Mar. 26, 2013, the entirety of each of which are incorporated herein by reference.

1. FIELD

Provided herein are solid forms comprising 4-amino-2-(2,6-dioxopiperidine-3-yl)isoindoline-1,3-dione and a coformer. Pharmaceutical compositions comprising such solid forms (e.g., cocrystals) and methods of use for treating, preventing, and managing various disorders are also provided herein.

2. BACKGROUND

2.1 Solid Forms of Pharmaceutical Compounds

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir™, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species may be termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement.

Cocrystals are crystalline molecular complexes of two or more non-volatile compounds bound together in a crystal lattice by non-ionic interactions. Pharmaceutical cocrystals are cocrystals of a therapeutic compound, e.g., an active pharmaceutical ingredient (API), and one or more non-volatile compound(s) (referred to herein as coformer). A coformer in a pharmaceutical cocrystal is typically a non-toxic pharmaceutically acceptable molecule, such as, for example, food additives, preservatives, pharmaceutical excipients, or other APIs. In recent years, pharmaceutical cocrystals have emerged as a possible alternative approach to enhance physicochemical properties of drug products.

The variety of possible solid forms creates potential diversity in physical and chemical properties for a given pharmaceutical compound. The discovery and selection of solid forms are of great importance in the development of an effective, stable and marketable pharmaceutical product.

2.2 Pomalidomide

Pomalidomide, which was previously referred to as CC-4047, and has a chemical name of 4-amino-2-(2,6-dioxopiperidine-3-yl)isoindoline-1,3-dione. Pomalidomide is a compound that inhibits, for example, LPS induced monocyte TNFα, IL-1β, IL-12, IL-6, MIP-1, MCP-1, GM-CSF, G-CSF, and COX-2 production, and may be used in treating various disorders. See, e.g., U.S. Pat. Nos. 5,635,517, 6,316,471, 6,476,052, 7,393,863, 7,629,360, and 7,863,297; and U.S. Patent Application Publication Nos. 2005/0143420, 2006/0166932, 2006/0188475, 2007/0048327, 2007/0066512, 2007/0155791, 2008/0051431, 2008/0317708, 2009/0087407, 2009/0088410, 2009/01317385, 2009/0148853, 2009/0232776, 2009/0232796, 2010/0098657, 2010/0099711, and 2011/0184025, the entireties of which are incorporated herein by reference. The compound is also known to co-stimulate the activation of T-cells. Pomalidomide has direct anti-myeloma tumoricidal activity, immunomodulatory activities and inhibits stromal cell support for multiple myeloma tumor cell growth. Specifically, pomalidomide inhibits proliferation and induces apoptosis of hematopoietic tumor cells. Id. Additionally, pomalidomide inhibits the proliferation of lenalidomide-resistant multiple myeloma cell lines and synergizes with dexamethasone in both lenalidomide-sensitive and lenalidomide-resistant cell lines to induce tumor cell apoptosis. Pomalidomide enhances T cell- and natural killer (NK) cell-mediated immunity, and inhibits production of pro-inflammatory cytokines (e.g., TNF-α and IL-6) by monocytes. Pomalidomide also inhibits angiogenesis by blocking the migration and adhesion of endothelial cells. Due to its diversified pharmacological properties, pomalidomide is useful in treating, preventing, and/or managing various diseases or disorders.

Pomalidomide and methods of synthesizing the compound are described, e.g., in U.S. Pat. Nos. 5,635,517, 6,335,349, 6,316,471, 6,476,052, 7,041,680, 7,709,502, and 7,994,327; and U.S. Patent Application Publication Nos. 2006/0178402 and 2011/0224440; the entireties of which are incorporated herein by reference.

Citation of any references in this Section is not to be construed as an admission that such references are prior art to the present application.

3. SUMMARY

Provided herein are solid forms (e.g., crystal forms or amorphous forms, or mixtures thereof) comprising pomalidomide, or pharmaceutically acceptable salts, stereoisomers, solvates (including, hydrates), prodrugs, or clathrates thereof, and a coformer. Also provided are methods of preparing, isolating, and characterizing the solid forms.

Also provided herein are pharmaceutical compositions and single unit dosage forms, which comprise one or more solid forms provided herein.

Also provided herein are methods of treating and managing various diseases or disorders. The methods comprise administering to a patient in need of such treatment or management a therapeutically effective amount of a solid form provided herein.

Also provided herein are methods of preventing various diseases and disorders, which comprise administering to a patient in need of such prevention a prophylactically effective amount of a solid form provided herein.

The various diseases and disorders include, but are not limited to: cancer, including hematologic cancer or solid tumor, for example, multiple myeloma, leukemia, lymphoma, sarcoma, prostate cancer, or small cell lung cancer; scleroderma; amyloidosis; pain; myelofibrosis; myeloproliferative disease, for example, myelofibrosis with myeloid metaplasia (MMM); myelodysplastic syndromes; diffuse systemic sclerosis; macular degeneration; a skin disease; a pulmonary disorder; an asbestos-related disorder; a parasitic disease; an immunodeficiency disorder; a CNS disorder; a CNS injury; atherosclerosis; hemoglobinopathy; anemia, for example, sickle cell anemia; an inflammatory disease; an autoimmune disease; a viral disease; a genetic disease; an allergic disease; a bacterial disease; an ocular neovascular disease; a choroidal neovascular disease; a retina neovascular disease; and rubeosis.

4. BRIEF DESCRIPTION OF THE DRAWINGS

FIG. 1 provides a representative X-ray Powder Diffraction (XRPD) pattern of one embodiment of a solid form comprising pomalidomide and gallic acid.

Figure 2:
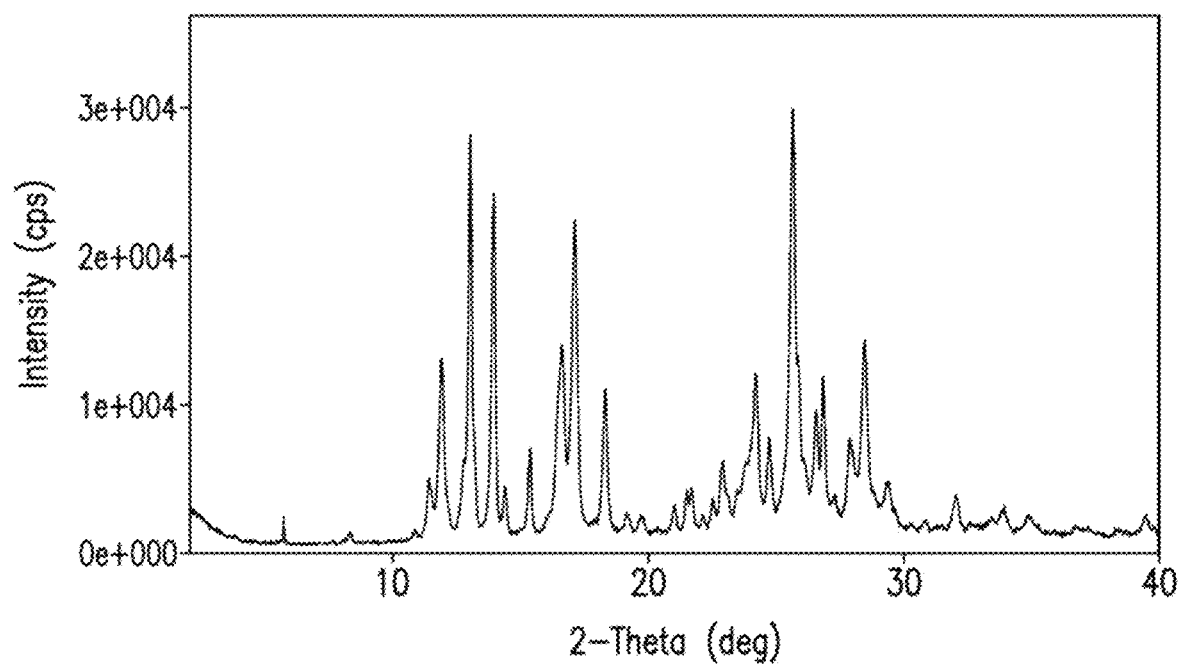

FIG. 2 provides a representative XRPD pattern of one embodiment of a solid form comprising pomalidomide and vanillin.

Figure 3:
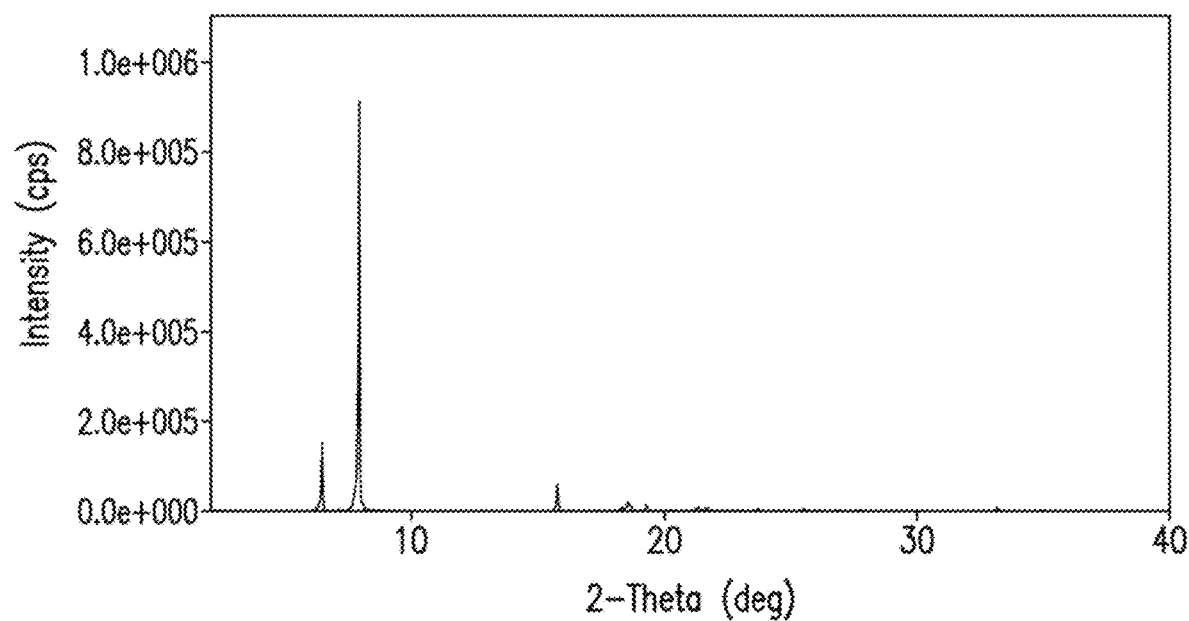

FIG. 3 provides a representative XRPD pattern of one embodiment of a solid form comprising pomalidomide and cyclamic acid.

Figure 4:
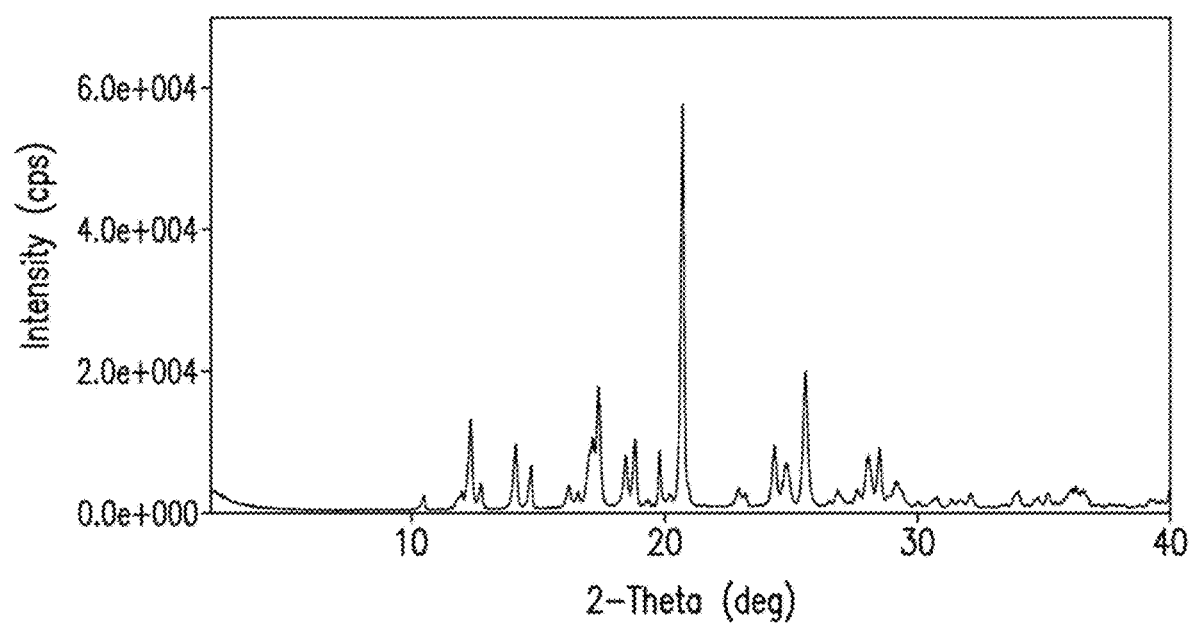

FIG. 4 provides a representative XRPD pattern of one embodiment of a solid form comprising pomalidomide and D-glucose.

Figure 5:
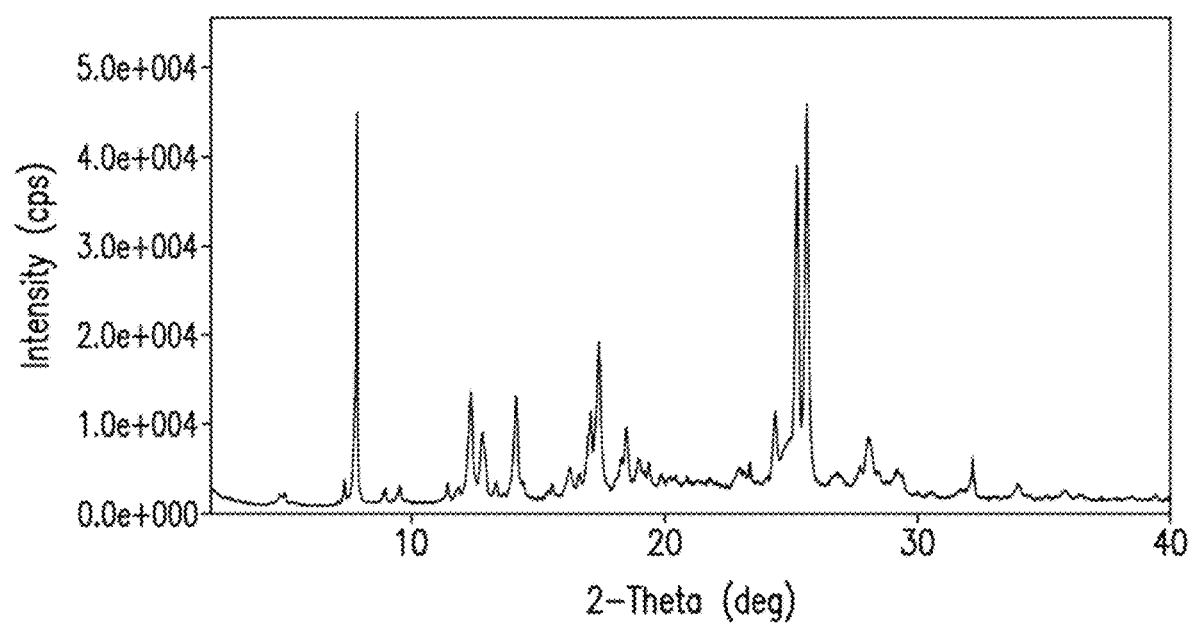

FIG. 5 provides a representative XRPD pattern of one embodiment of a solid form comprising pomalidomide and propyl gallate.

Figure 6:
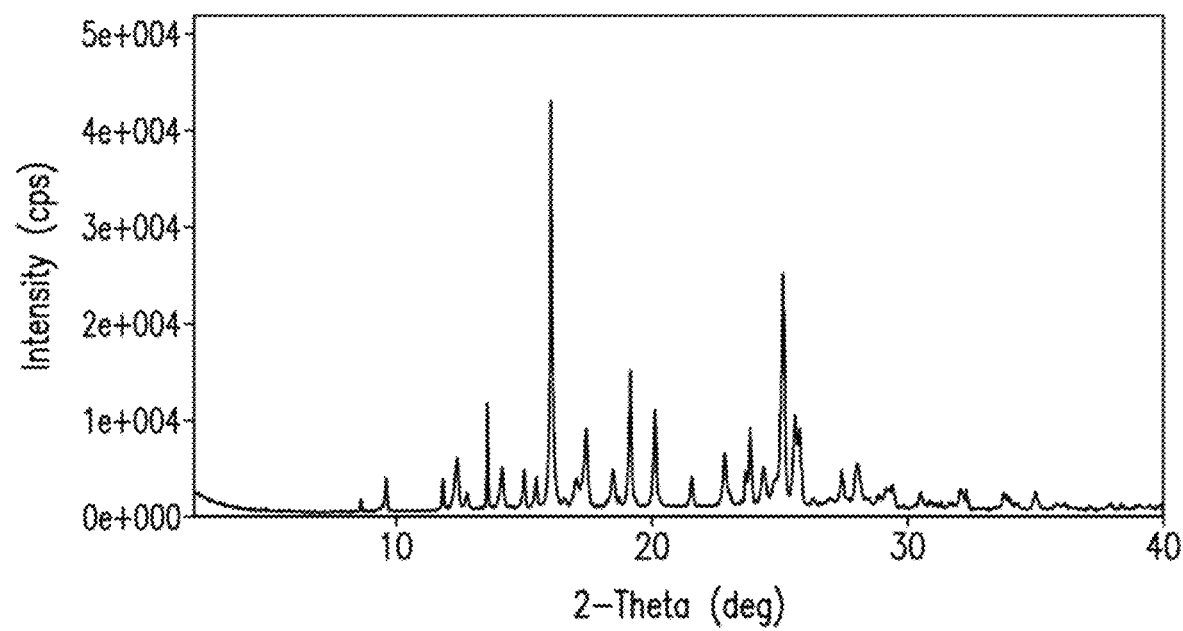

FIG. 6 provides a representative XRPD pattern of one embodiment of a solid form comprising pomalidomide and saccharin.

Figure 7:
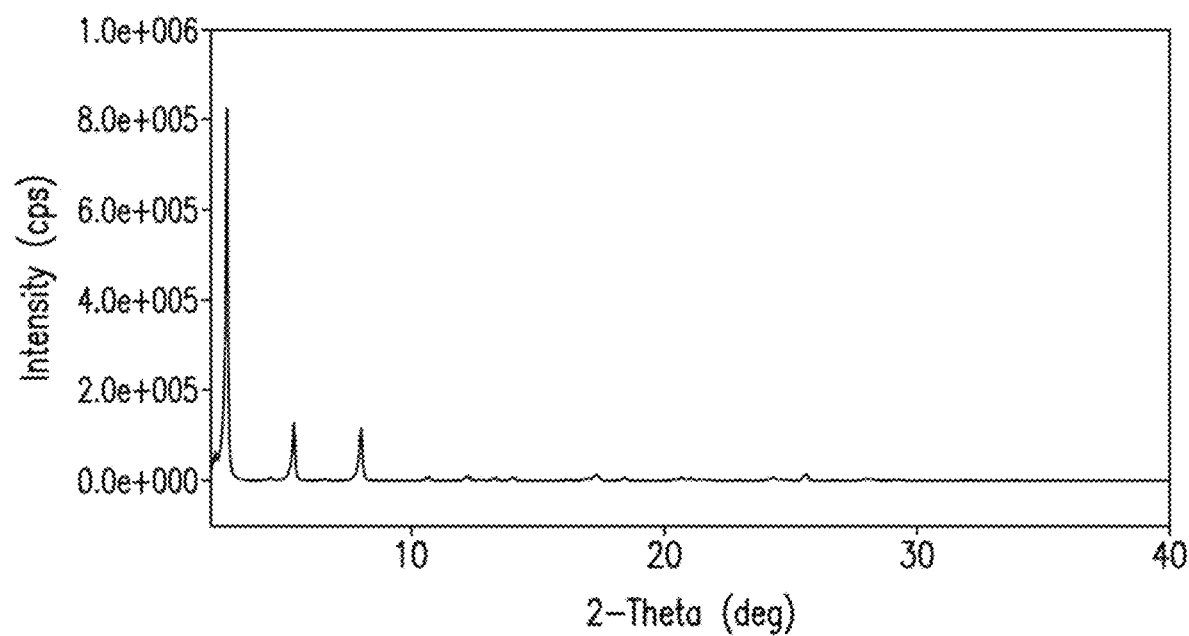

FIG. 7 provides a representative XRPD pattern of one embodiment of a solid form comprising pomalidomide and sodium lauryl sulfate.

Figure 8:
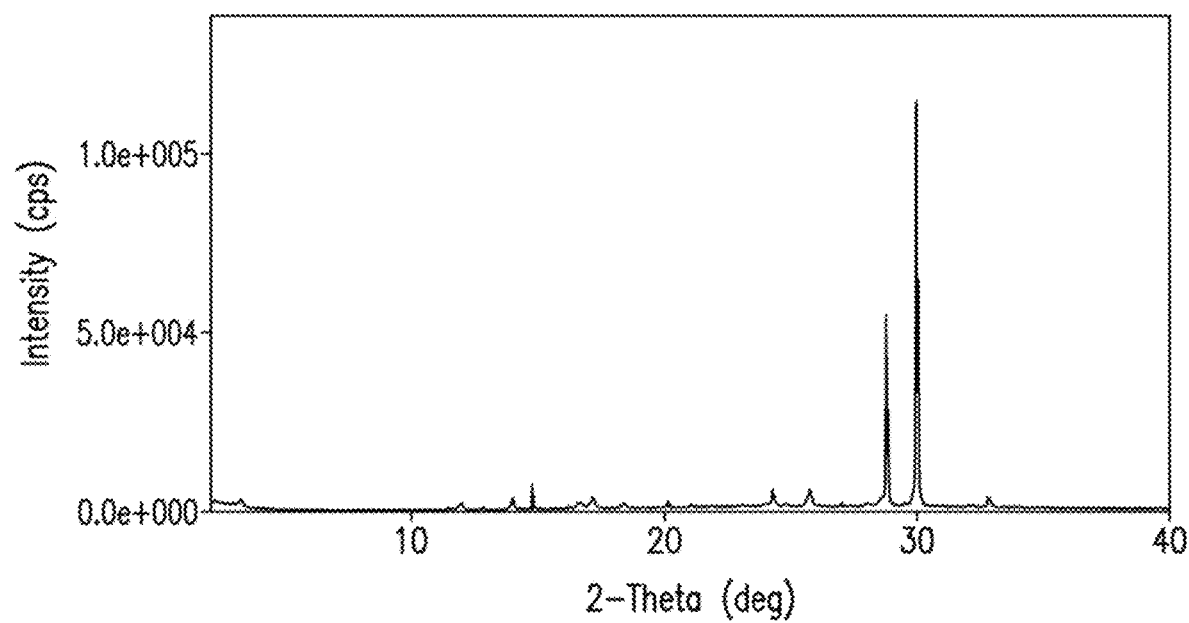

FIG. 8 provides a representative XRPD pattern of one embodiment of a solid form comprising pomalidomide and magnesium bromide.

Figure 9:
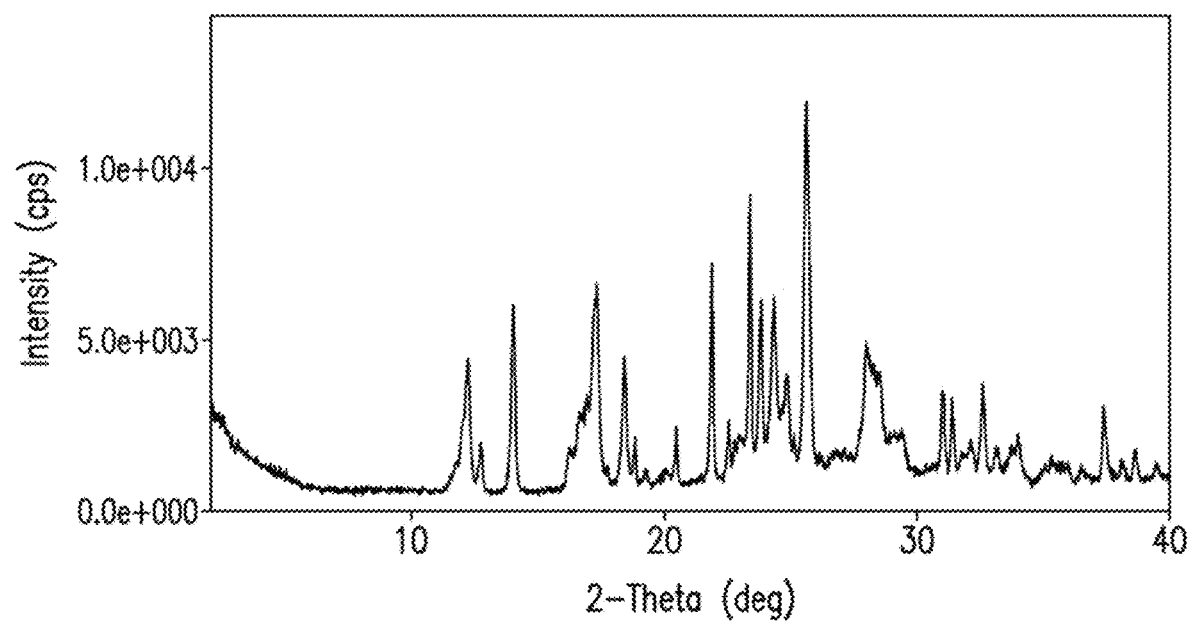

FIG. 9 provides a representative XRPD pattern of one embodiment of a solid form comprising pomalidomide and malonic acid.

Figure 10:
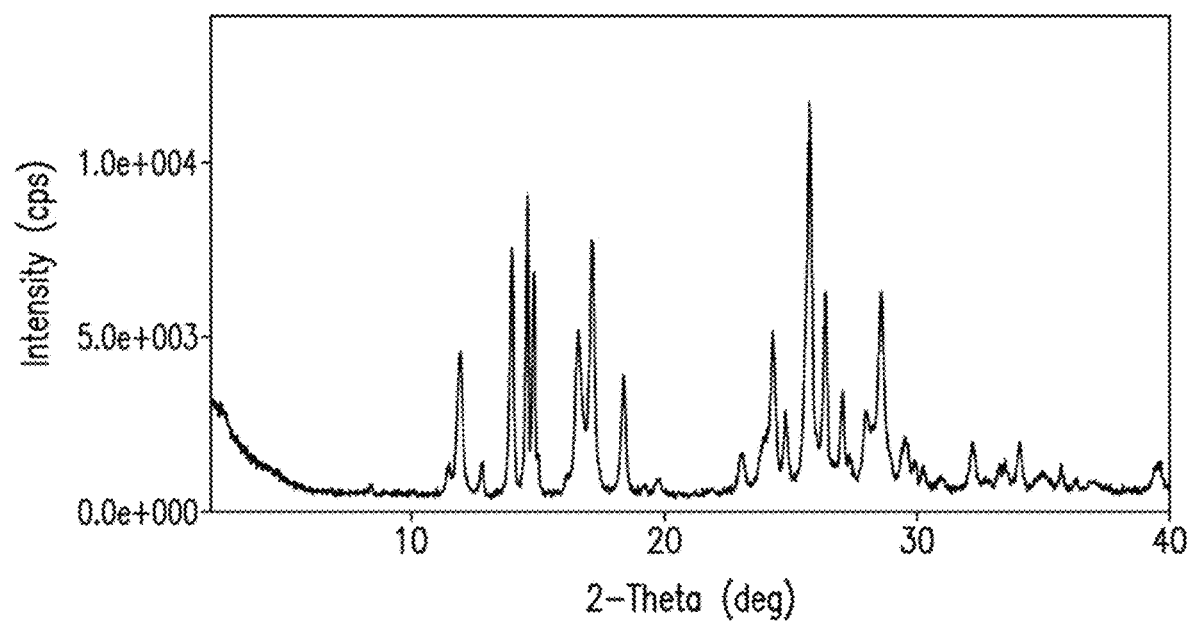

FIG. 10 provides a representative XRPD pattern of one embodiment of a solid form comprising pomalidomide and maltol.

Figure 11:
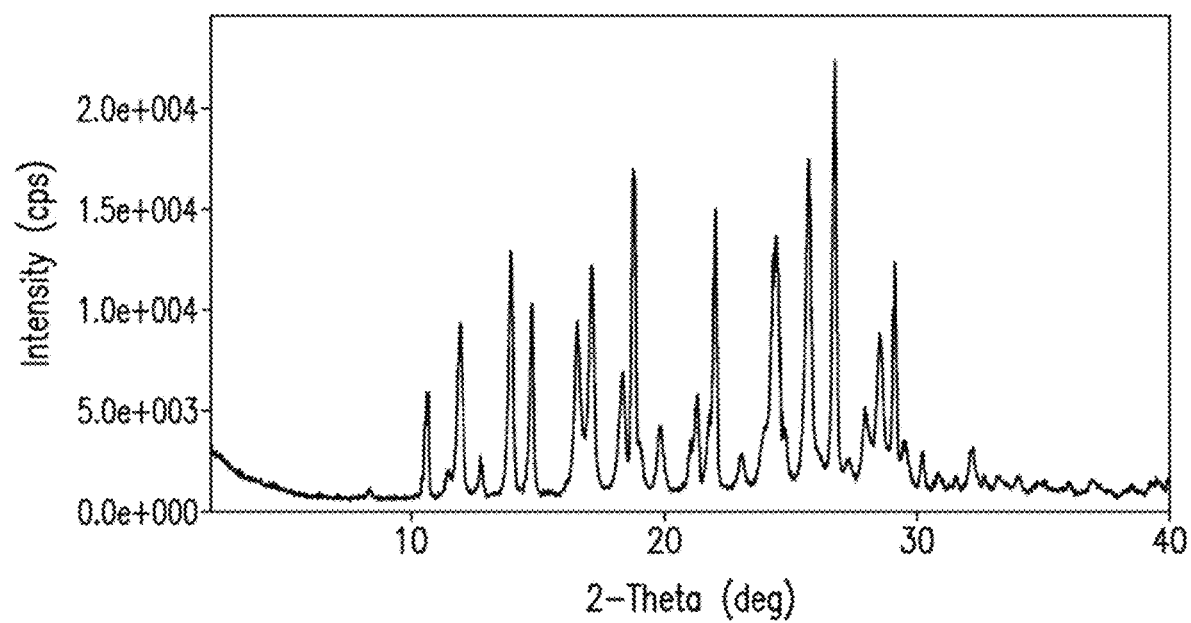

FIG. 11 provides a representative XRPD pattern of one embodiment of a solid form comprising pomalidomide and methyl paraben.

Figure 12:
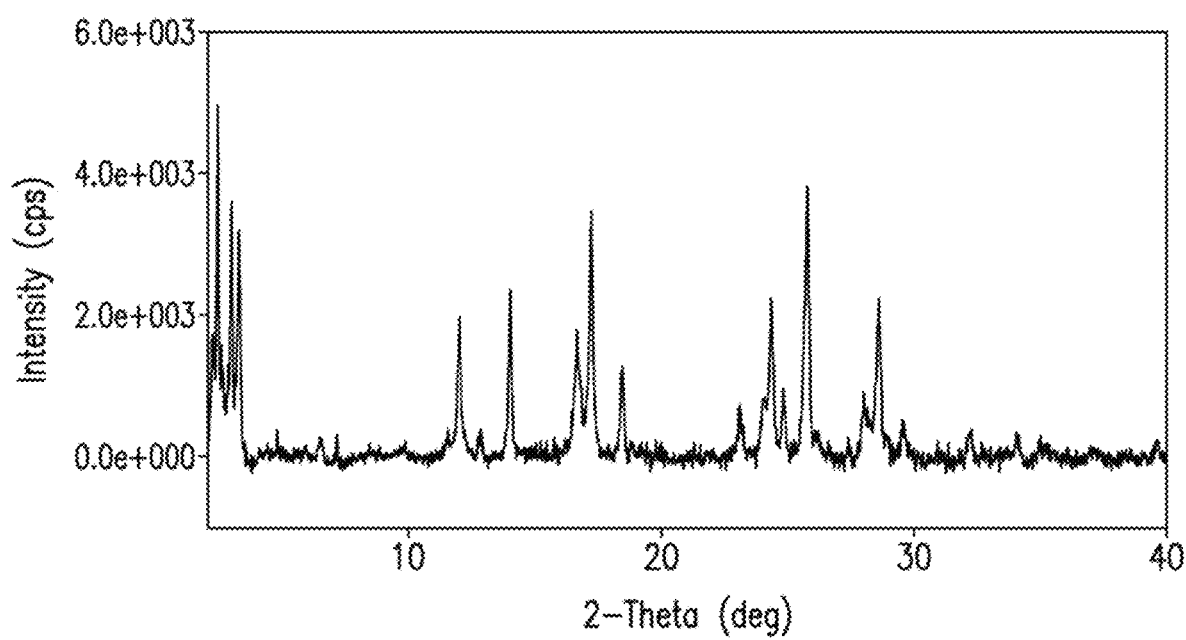

FIG. 12 provides a representative XRPD pattern of one embodiment of a solid form comprising pomalidomide and zinc chloride.

Figure 13A:
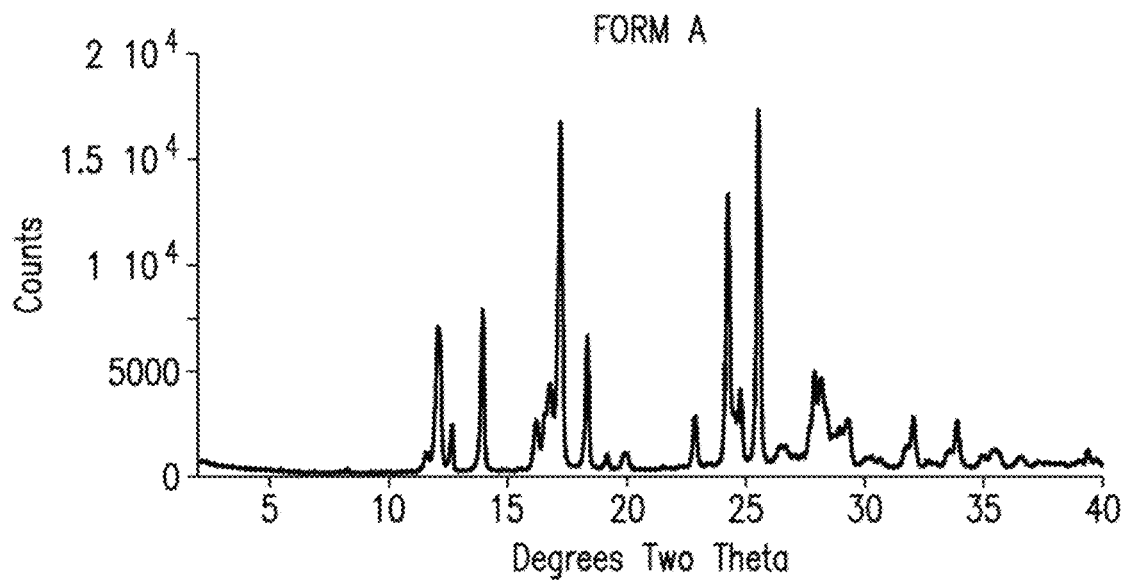

FIG. 13A provides a representative XRPD pattern of one embodiment of a solid form comprising Form A of pomalidomide.

Figure 13B:
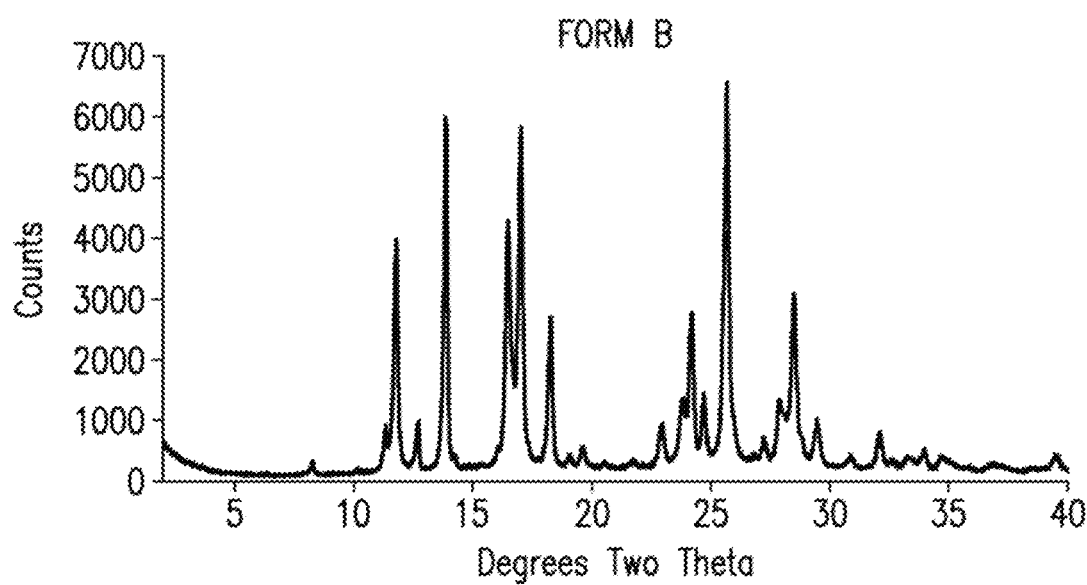

FIG. 13B provides a representative XRPD pattern of one embodiment of a solid form comprising Form B of pomalidomide.

Figure 14:
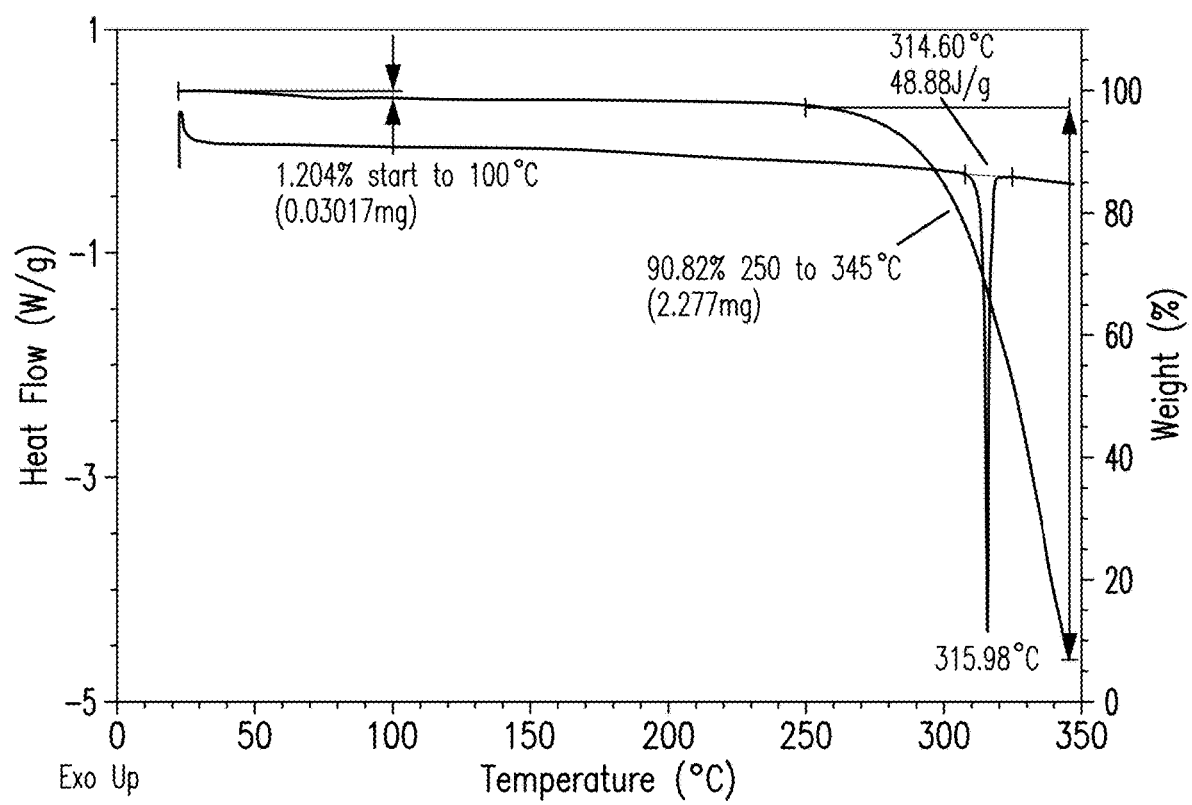

FIG. 14 provides a representative thermal gravimetric analysis (TGA) thermogram and a representative differential scanning calorimetry (DSC) thermogram of a solid form comprising Form B of pomalidomide.

5. DETAILED DESCRIPTION

5.1 Definitions

As used herein, and in the specification and the accompanying claims, the indefinite articles "a" and "an" and the definite article "the" include plural as well as single referents, unless the context clearly indicates otherwise.

As used herein, and unless otherwise specified, the compound referred to herein by the name pomalidomide, 4-amino-2-(2,6-dioxopiperidine-3-yl)isoindoline-1,3-dione, or CC-4047, corresponds to chemical structure (I), depicted below. In certain embodiments, the term pomalidomide, 4-amino-2-(2,6-dioxopiperidine-3-yl)isoindoline-1,3-dione, or CC-4047 may be used herein to refer to either a free base form or an ionized form of a compound of formula (I) (e.g., the molecule is protonated at one or more basic centers).

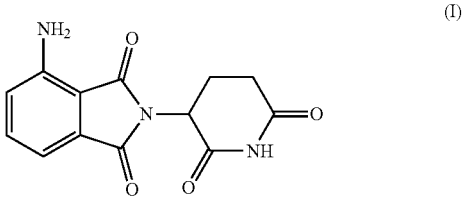 [SMILES: Nc1cccc2c1C(=O)N(C1CCC(=O)NC1=O)C2=O]

(I)

Unless otherwise specified, the terms "solid form," "solid forms," and related terms, when used herein to refer to pomalidomide, refer to a physical form comprising pomalidomide, which is not predominantly in a liquid or a gaseous state. As used herein, the terms "solid form" and "solid forms" encompass semi-solids. Solid forms may be crystalline, amorphous, partially crystalline, partially amorphous, or mixtures of forms. A "single-component" solid form comprising pomalidomide consists essentially of pomalidomide. A "multiple-component" solid form comprising pomalidomide comprises a significant quantity of one or more additional species, such as ions and/or molecules, within the solid form. For example, in particular embodiments, a crystalline multiple-component solid form comprising pomalidomide further comprises one or more species non-covalently bonded at regular positions in the crystal lattice.

Unless otherwise specified, the term "crystalline" and related terms used herein, when used to describe a substance, component, product, or form, mean that the substance, component, product, or form is substantially crystalline, for example, as determined by X-ray diffraction. (see, e.g., *Remington's Pharmaceutical Sciences*, 18$^{th}$ ed., Mack Publishing, Easton Pa., 173 (1990); *The United States Pharmacopeia*, 23$^{rd}$ ed., 1843-1844 (1995)).

Unless otherwise specified, the term "crystal form," "crystal forms," and related terms herein refer to crystalline modifications comprising a given substance, including single-component crystal forms and multiple-component crystal forms, and including, but not limited to, polymorphs, solvates, hydrates, co-crystals, other molecular complexes, salts, solvates of salts, hydrates of salts, co-crystals of salts, and other molecular complexes of salts, and polymorphs thereof. In some embodiments, a crystal form of a substance may be substantially free of amorphous forms and/or other crystal forms. In other embodiments, a crystal form of a substance may contain less than about 1%, 2%, 3%, 4%, 5%, 10%, 15%, 20%, 25%, 30%, 35%, 40%, 45%, or 50% of one or more amorphous form(s) and/or other crystal form(s) on a weight basis. Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Unless otherwise specified, the term "cocrystal" or "co-crystal," as used herein, refers to a crystalline material comprised of two or more non-volative compounds bond together in a crystal lattice by non-covalent interactions.

Unless otherwise specified, the term "pharmaceutical cocrystal" or "cocrystal" of an active pharmaceutical ingredient (API), as used herein, refers to a crystalline material comprised of an API and one or more non-volatile compound(s) (referred herein as a coformer). The API and the coformer interact through non-covalent forces in a crystal lattice.

Unless otherwise specified, the term "amorphous," "amorphous form," and related terms used herein mean that the substance, component, or product referred to is not substantially crystalline as determined by X-ray diffraction. In certain embodiments, an amorphous form of a substance may be substantially free of crystal forms. In other embodiments, an amorphous form of a substance may contain less than about 1%, 2%, 3%, 4%, 5%, 10%, 15%, 20%, 25%, 30%, 35%, 40%, 45% or 50% of one or more crystal forms on a weight basis. In other embodiments, an amorphous form of a substance may comprise additional components or ingredients (for example, an additive, a polymer, or an excipient that may serve to further stabilize the amorphous form). In some embodiments, amorphous form may be a solid solution. Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR)

and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2 degrees two theta while still describing the particular XRPD peak.

As used herein, and unless otherwise specified, a crystalline or amorphous form that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, and unless otherwise specified, the term "pharmaceutically acceptable salts" refers to salts prepared from pharmaceutically acceptable, relatively non-toxic acids, including inorganic acids and organic acids. In some embodiments, suitable acids include, but are not limited to, acetic, benzenesulfonic, benzoic, camphorsulfonic, carbonic, citric, dihydrogenphosphoric, ethenesulfonic, fumaric, galactunoric, gluconic, glucuronic, glutamic, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, nitric, pamoic, pantothenic, phosphoric, phthalic, propionic, suberic, succinic, sulfuric, tartaric, toluenesulfonic acid (including p-toluenesulfonic, m-toluenesulfonic, and o-toluenesulfonic acids), and the like (see, e.g., S. M. Berge et al., *J. Pharm. Sci.*, 66:1-19 (1977); and *Handbook of Pharmaceutical Salts: Properties, Selection and Use*, P. H. Stahl and C. G. Wermuth, Eds., (2002), Wiley, Weinheim). In some embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridine-sulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, co-crystal, or molecular complex. The terms "hydrate" and "hydrated," as used herein, can also refer to a hydrate of a salt, co-crystal, or molecular complex.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of a disease or disorder provided herein. The terms encompass the inhibition or reduction of a symptom of a particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread, or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease or one or more symptoms thereof.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, that provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or one or more symptoms thereof, or prevent the recurrence of the disease or disorder, or one or more symptoms thereof. A prophylactically effective amount of a compound means an amount of therapeutic agent, alone or in combination with other agents, that provides a prophylactic benefit in the prevention of the disease or disorder. The term "prophylactically effective amount" can encompass an amount that improves overall prophylaxis or enhances the prophylactic efficacy of another prophylactic agent.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

Unless otherwise specified, the term "therapeutically and prophylactically effective amount" refers to the amount of the subject solid form that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Unless otherwise specified, the term "subject" is defined herein to include animals, such as mammals, including, but not limited to, primates (e.g., humans), cows, sheep, goats, horses, dogs, cats, rabbits, rats, mice, and the like. In specific embodiments, the subject is a human.

Unless otherwise specified, to the extent that there is a discrepancy between a depicted chemical structure of a compound provided herein and a chemical name of a compound provided herein, the chemical structure shall control.

5.2 Solid Forms Comprising Pomalidomide and a Coformer

In one embodiment, provided herein are solid forms (e.g., crystal forms, amorphous forms, or mixtures thereof) comprising (a) pomalidomide, or a pharmaceutically acceptable salt, solvate, hydrate, stereoisomer, prodrug, or clathrate thereof; and (b) a coformer. In one embodiment, provided herein are solid forms (e.g., crystal forms, amorphous forms, or mixtures thereof) comprising (a) a free base of pomalidomide, or a solvate, hydrate, stereoisomer, prodrug, or clathrate thereof; and (b) a coformer. Pomalidomide can be synthesized or obtained according to a method known in the literature or based upon the teachings herein, including the methods described in detail in the examples herein.

In one embodiment, pomalidomide can be prepared according to methods described in, for example, U.S. Pat. Nos. 5,635,517, 6,335,349, 6,316,471, 6,476,052, 7,041,680, 7,709,502, and 7,994,327; and U.S. Patent Application Publication Nos. 2006/0178402 and 2011/0224440; the entireties of which are incorporated herein by reference.

The coformer can be any pharmaceutically acceptable coformer known in the art. In one embodiment, the coformer is acetylsalicylic acid, D-glucose, nicotinic acid, aconitic acid, L-glutamic acid, oxalic acid, adipic acid, glutaric acid, L-proline, 4-aminosalicylic acid, glycine, propyl gallate, L-ascorbic acid, glycolic acid, L-pyroglutamic acid, benzoic acid, hippuric acid, saccharin, (+)-camphoric acid, 1-hydroxy-2-naphthoic acid, salicylic acid, capric acid, ketoglutaric acid, sebacic acid, cinnamic acid, L-lysine, sodium lauryl sulfate, citric acid, magnesium bromide, sorbic acid, cyclamic acid, maleic acid, succinic acid, ethyl maltol, L-malic acid, L-tartaric acid, ethyl paraben, malonic acid, urea, D-fructose, maltol, vanillic acid, fumaric acid, D,L-mandelic acid, vanillin, gallic acid, methyl paraben, zinc chloride, gentisic acid, or nicotinamide.

In one embodiment, the coformer is gallic acid, vanillin, cyclamic acid, D-glucose, magnesium bromide, malonic acid, maltol, methyl paraben, propyl gallate, saccharin, sodium lauryl sulfate, or zinc chloride.

In one embodiment, solid forms provided herein may be a crystal form or an amorphous form or mixtures thereof (e.g., mixtures of crystal forms, or mixtures of crystal and amorphous forms), which comprises (a) pomalidomide or a pharmaceutically acceptable salt, solvate, hydrate, stereoisomer, prodrug, or clathrate thereof and (b) a coformer. In one embodiment, provided herein is a crystal form comprising (a) pomalidomide or a pharmaceutically acceptable salt, solvate, hydrate, stereoisomer, prodrug, or clathrate thereof and (b) a coformer. In one embodiment, provided herein is a cocrystal comprising (a) pomalidomide or a pharmaceutically acceptable salt, solvate, hydrate, stereoisomer, prodrug, or clathrate thereof and (b) a coformer. In one embodiment, provided herein is an amorphous form comprising (a) pomalidomide or a pharmaceutically acceptable salt, solvate, hydrate, stereoisomer, prodrug, or clathrate thereof and (b) a coformer. In one embodiment, provided herein is a mixture comprising (i) a cocrystal comprising (a) pomalidomide or a pharmaceutically acceptable salt, solvate, hydrate, stereoisomer, prodrug, or clathrate thereof and (b) a coformer; and (ii) a crystal form of pomalidomide or a pharmaceutically acceptable salt, solvate, hydrate, stereoisomer, prodrug, or clathrate thereof. In one embodiment, provided herein is a mixture comprising (i) a cocrystal comprising (a) pomalidomide or a pharmaceutically acceptable salt, solvate, hydrate, stereoisomer, prodrug, or clathrate thereof and (b) a coformer; and (ii) an amorphous form of pomalidomide or a pharmaceutically acceptable salt, solvate, hydrate, stereoisomer, prodrug, or clathrate thereof.

In one embodiment, provided herein is an unsolvated solid form comprising (a) pomalidomide and (b) a coformer. In one embodiment, provided herein is an anhydrous solid form comprising (a) pomalidomide and (b) a coformer. In one embodiment, provided herein is an unsolvated crystal form comprising (a) pomalidomide and (b) a coformer. In one embodiment, provided herein is an anhydrous crystal form comprising (a) pomalidomide and (b) a coformer. In one embodiment, provided herein is an unsolvated amorphous form comprising (a) pomalidomide and (b) a coformer. In one embodiment, provided herein is an anhydrous amorphous form comprising (a) pomalidomide and (b) a coformer. In one embodiment, provided herein is a solvated solid form comprising (a) pomalidomide and (b) a coformer. In one embodiment, provided herein is a hydrated solid form comprising (a) pomalidomide and (b) a coformer (e.g., a hydrate having a stoichiometric or non-stoichiometric amount of water). In one embodiment, provided herein is a hydrated form of (a) pomalidomide and (b) a coformer, including, but not limited to, a hemihydrate, a monohydrate, a dihydrate, a trihydrate, and the like. In one embodiment, the hydrated form is substantially crystalline. In one embodiment, the hydrated form is substantially amorphous. In one embodiment, the anhydrous form is substantially crystalline. In one embodiment, the anhydrous form is substantially amorphous. In one embodiment, provided herein is an unsolvated cocrystal comprising (a) pomalidomide and (b) a coformer. In one embodiment, provided herein is an anhydrous cocrystal comprising (a) pomalidomide and (b) a coformer. In one embodiment, provided herein is a hydrated cocrystal comprising (a) pomalidomide and (b) a coformer. In one embodiment, provided herein is a solvated cocrystal comprising (a) pomalidomide and (b) a coformer.

Solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In another embodiment, provided herein are compositions comprising one or more solid form(s) comprising (a) pomalidomide or a pharmaceutically acceptable salt, solvate, hydrate, stereoisomer, prodrug, or clathrate thereof; and (b) a coformer. Also provided herein are compositions comprising: (i) one or more solid form(s) provided herein (e.g., one or more crystal forms, one or more amorphous forms, and mixtures thereof), and (ii) other active ingredient(s). Also provided herein are methods of using these compositions in the treatment, prevention, or management of conditions and disorders including, but not limited to: cancer, including hematologic cancer or solid tumor, for example, multiple myeloma, leukemia, lymphoma, sarcoma, prostate cancer, or small cell lung cancer; scleroderma; amyloidosis; pain; myelofibrosis; myeloproliferative disease, e.g., MMM; myelodysplastic syndromes; diffuse systemic sclerosis; macular degeneration; a skin disease; a pulmonary disorder; an asbestos-related disorder; a parasitic disease; an immunodeficiency disorder; a CNS disorder; a CNS injury; atherosclerosis; hemoglobinopathy; anemia, e.g., sickle cell anemia; an inflammatory disease; an autoimmune disease; a viral disease; a genetic disease; an allergic disease; a bacterial disease; an ocular neovascular disease; a choroidal neovascular disease; a retina neovascular disease; and rubeosis.

While not intending to be bound by any particular theory, certain solid forms provided herein exhibit physical properties, e.g., stability, solubility and/or dissolution rate, appropriate for use in clinical and therapeutic dosage forms. Moreover, while not wishing to be bound by any particular theory, certain solid forms provided herein exhibit physical properties, e.g., crystal morphology, compressibility and/or hardness, suitable for manufacture of a solid dosage form. In some embodiments, such properties can be determined using techniques such as X-ray diffraction, microscopy, IR spectroscopy and thermal analysis, as described herein and known in the art.

Certain embodiments herein provide solid forms comprising (a) pomalidomide and (b) a coformer. In one embodiment, provided herein is a solid form comprising (a) pomalidomide and (b) a coformer that is substantially crystalline. In one embodiment, provided herein is a cocrystal comprising (a) pomalidomide and (b) a coformer. In one embodiment, provided herein is a solid form comprising a cocrystal comprising (a) pomalidomide and (b) a coformer. In one embodiment, provided herein is a solid form comprising (i) a cocrystal comprising (a) pomalidomide and (b) a coformer and (ii) an amorphous form of pomalidomide. In one embodiment, provided herein is a solid form comprising (i) a cocrystal comprising (a) pomalidomide and (b) a coformer and (ii) one or more additional crystal forms of pomalidomide.

In some embodiments, the cocrystal comprising (a) pomalidomide and (b) a coformer can be obtained by crystallization from certain solvent systems, for example, solvent systems comprising one or more of the following solvents: acetone, N,N-dimethylformamide (DMF), tetrahydrofuran (THF), and methanol. Other examples of solvent systems are provided herein elsewhere. In certain embodiments, a solid form provided herein (e.g., a cocrystal comprising (a) pomalidomide and (b) a coformer) can be obtained by slurry crystallization, evaporation crystallization, cooling crystallization, and precipitation crystallization.

In certain embodiments, the non-covalent forces are one or more hydrogen bonds (H-bonds). The coformer may be H-bonded directly to the API or may be H-bonded to an additional molecule which is bound to the API. The additional molecule may be H-bonded to the API or bound ionically or covalently to the API. The additional molecule could also be a different API. In certain embodiments, the co-crystals may include one or more solvate molecules in the crystalline lattice, i.e., solvates of co-crystals, or a co-crystal further comprising a solvent or compound that is a liquid at room temperature. In certain embodiments, the co-crystals may be a co-crystal between a coformer and a salt of an API. In certain embodiments, the non-covalent forces are pi-stacking, guest-host complexation and/or van der Waals interactions. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

In certain embodiments, the coformer is a solid under ambient temperature conditions when in its pure form. In certain embodiments, the coformer is selected from acetylsalicylic acid, D-glucose, nicotinic acid, aconitic acid, L-glutamic acid, oxalic acid, adipic acid, glutaric acid, L-proline, 4-aminosalicylic acid, glycine, propyl gallate, L-ascorbic acid, glycolic acid, L-pyroglutamic acid, benzoic acid, hippuric acid, saccharin, (+)-camphoric acid, 1-hydroxy-2-naphthoic acid, salicylic acid, capric acid, ketoglutaric acid, sebacic acid, cinnamic acid, L-lysine, sodium lauryl sulfate, citric acid, magnesium bromide, sorbic acid, cyclamic acid, maleic acid, succinic acid, ethyl maltol, L-malic acid, L-tartaric acid, ethyl paraben, malonic acid, urea, D-fructose, maltol, vanillic acid, fumaric acid, D,L-mandelic acid, vanillin, gallic acid, methyl paraben, zinc chloride, gentisic acid, and nicotinamide. In certain embodiments, the coformer is a second API.

In certain embodiments, the co-crystals include an acid addition salt or base addition salt of an API. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g., isopropylamine, trimethyl amine, diethyl amine, tri(isopropyl) amine, tri(n-propyl) amine, ethanolamine, 2-dimethylaminoethanol, tromethamine, lysine, arginine, histidine, procaine, hydrabamine, choline, betaine, ethylenediamine, glucosamine, N-alkylglucamines, theobromine, purines, piperazine, piperidine, morpholine, and N-ethylpiperidine).

The ratio of API to coformer may be stoichiometric or non-stoichiometric. In one embodiment, the ratio of API to coformer is about 5:1, 4:1, 3:1, 2.5:1, 2:1, 1.5:1, 1:1, 1:1.5, 1:2, 1:2.5, 1:3, 1:4, or 1:5. In one embodiment, the ratio of API to coformer is about 1:1. In one embodiment, the co-crystal comprises more than one coformers. In one embodiment, the co-crystal comprises two coformers.

In certain embodiments, cocrystals can be prepared using solid-state methods such as solid-state grinding and solvent-drop grinding. In certain embodiments, cocrystals can be prepared using high-throughput screening. In certain embodiments cocrystals can be prepared using solution-based crystallization.

In certain embodiments, cocrystals formation can lead to enhancement of physical properties of the resulting solid forms, such as solubility, dissolution rate, bioavailability, physical stability, chemical stability, flowability, fractability, or compressibility. In certain embodiments, a given API may form different cocrystals with many different counter-molecules, and some of these cocrystals may exhibit enhanced solubility or stability. In certain embodiments pharmaceutical cocrystals increase the bioavailability or stability profile of a compound without the need for chemical (covalent) modification of the API.

The compounds provide herein may also contain an unnatural proportion of an atomic isotope at one or more of the atoms that constitute such a compound. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the compounds provided herein, whether radioactive or not, are intended to be encompassed herein. In certain embodiments, a compound provided herein contains unnatural proportion(s) of one or more isotopes, including, but not limited to, hydrogen ($^1$H), deuterium ($^2$H), tritium ($^3$H), carbon-11 ($^{11}$C), (carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, a compound provided herein contains unnatural proportion(s) of one or more isotopes in a stable form, that is, non-radioactive, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, a compound provided herein contains unnatural proportion(s), of one or more isotopes in an unstable form, that is, radioactive, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). In certain embodiments, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, a compound provided herein contains unnatural proportions of deuterium (D). In exemplary embodiments, provided herein are isotopologues of pomalidomide, as disclosed in U.S. Provisional Application No. 61/500,053, filed Jun. 22, 2011, which is incorporated by reference herein in its entirety. In one embodiment, provided herein are solid forms (e.g., crystal forms, amorphous forms, or mixtures thereof) of isotopologues of pomalidomide provided herein.

In certain embodiments, slurry crystallization is effected by adding solvent or solvent mixtures to a solid substrate, and the slurry is stirred, and optionally heated to various temperatures. In certain embodiments, the slurry is heated at about 25° C., about 50° C., about 80° C., or about 100° C. In certain embodiments, upon heating and cooling, the residual solvents of the slurry can be removed by wicking, or other suitable methods, such as filtration, centrifugation, or decantation, and the crystals can be dried in air or under vacuum.

In certain embodiments, evaporation crystallization is effected by adding a solvent or solvent mixture to a solid substrate, and allowing the solvent or solvent mixture to evaporate under ambient conditions. In certain embodiments, the residual solvent can be removed by wicking, or other suitable methods, such as filtration, centrifugation, or decantation, and the crystals can be dried in air or under vacuum.

In certain embodiments, precipitation crystallization is effected by adding a solvent or solvent mixture to a solid substrate, and subsequently adding an anti-solvent. In certain embodiments, the resultant mixture stands for a period of time, e.g., overnight, and under certain conditions, for example at room temperature. In certain embodiments, the residual solvent can be removed by wicking, or other suitable methods, such as filtration, centrifugation, or decantation, and the crystals can be dried in air or under vacuum.

In certain embodiments, cooling crystallization is effected by adding a solvent or solvent mixture to a solid substrate at elevated temperature, and allowing the resultant mixture to stand for a period of time at a reduced temperature. In certain embodiments, the elevated temperature is, for example, about 30° C., about 40° C., about 50° C., about 60° C., about 70° C., or about 80° C. In certain embodiments, the reduced temperature is, for example, about 15° C., about 10° C., about 5° C., about 0° C., about −5° C., about −10° C., about −15° C., or about −20° C. The residual solvent can be removed by wicking, or other suitable methods, such as filtration, centrifugation, or decantation, and the crystals can be dried in air or under vacuum.

5.2.1 Cocrystal Comprising Pomalidomide and Gallic Acid

Certain embodiments herein provide solid forms comprising pomalidomide and gallic acid. In one embodiment, provided herein is a solid form comprising pomalidomide and gallic acid that is substantially crystalline. In one embodiment, provided herein is a cocrystal comprising pomalidomide and gallic acid. In one embodiment, provided herein is a solid form comprising a cocrystal comprising pomalidomide and gallic acid. In one embodiment, provided herein is a solid form comprising (i) a cocrystal comprising pomalidomide and gallic acid and (ii) an amorphous form of pomalidomide. In one embodiment, provided herein is a solid form comprising (i) a cocrystal comprising pomalidomide and gallic acid and (ii) one or more additional crystal forms of pomalidomide. Provided herein are various embodiments, preparations, or modifications of a cocrystal comprising pomalidomide and gallic acid.

In some embodiments, the cocrystal comprising pomalidomide and gallic acid is obtained by mixing pomalidomide and gallic acid in a solvent system. In some embodiments, the cocrystal is obtained by mixing pomalidomide and gallic acid in a solvent system saturated with gallic acid. In some embodiments, the cocrystal is obtained by mixing pomalidomide and gallic acid in a solvent system saturated with gallic acid, and subsequently stirring the mixture at room temperature for about 24 hours. In some embodiments, the cocrystal is obtained by mixing pomalidomide and gallic acid in a solvent system saturated with gallic acid, subsequently stirring the mixture at room temperature for about 24 hours, and isolating the solid by centrifugation. In some embodiments, the cocrystal is obtained by mixing approximately equal molar amount of pomalidomide and gallic acid in a solvent system saturated with gallic acid. In some embodiments, the solvent system is a mixed solvent of DMF and acetone. In some embodiments, the solvent system is a mixed solvent of DMF and acetone with a volumn ratio of DMF to acetone of about 1:2.

In some embodiments, the cocrystal comprising pomalidomide and gallic acid is obtained by removing solvent from a solution containing pomalidomide and gallic acid. In some embodiments, the cocrystal is obtained by removing solvent from a solution containing pomalidomide and gallic acid on a rotary evaporator at about 65° C. In some embodiments, the cocrystal is obtained by removing solvent from a solution containing pomalidomide and gallic acid, and subsequently storing the residue at about 75% relative humidity for 1 day. In some embodiments, the cocrystal is obtained by removing solvent from a solution containing pomalidomide and gallic acid, and subsequently storing the residue at about 60° C. overnight. In some embodiments, the cocrystal is obtained by removing solvent from a solution containing approximately equal molar amount of pomalidomide and gallic acid. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and gallic acid with a molar ratio of pomalidomide to gallic acid of approximately 2:1 to 1:2. In some embodiments, the molar ratio of pomalidomide to gallic acid is approximately 1:1.

A representative XRPD pattern of a solid form comprising pomalidomide and gallic acid is provided in FIG. 1. In some embodiments, provided herein is a solid form comprising pomalidomide and gallic acid characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 9.75, 10.77, 11.75, 12.29, 12.73, 13.22, 14.06, 15.11, 15.52, 16.16, 16.59, 16.94, 17.34, 18.42, 19.32, 19.38, 20.20, 21.52, 21.80, 22.98, 23.20, 24.28, 24.82, 25.56, 26.16, 26.90, 27.99, 29.20, 30.40, 31.31, 32.06, 32.59, 32.82, 33.87, 34.67, 35.10, 36.66, 37.16, 38.46, 39.24, and 39.78 degrees 2θ, plus or minus 0.10. In some embodiments, provided herein is a solid form comprising pomalidomide and gallic acid characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 9.75, 10.77, 12.29, 14.06, 15.52, 16.16, 17.34, 18.42, 22.98, 23.20, 24.82, 25.56, 26.16, 26.90, 27.99, and 32.06 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and gallic acid having an XRPD pattern comprising peaks at approximately 22.98, 26.16, and 26.90 degrees 2θ. In certain embodiments, the solid form further comprises peaks at approximately 15.52, 18.42 and 23.20 degrees 2θ. In one embodiment, the solid form comprises peaks at approximately 9.75, 10.77, 12.29, 14.06, 15.52, 16.16, 17.34, 18.42, 22.98, 23.20, 24.82, 25.56, 26.16, 26.90, 27.99, and 32.06 degrees 2θ.

In some embodiments, provided herein is a solid form comprising pomalidomide and gallic acid having an XRPD pattern comprising peaks at approximately 15.52, 26.16, and 26.90 degrees 2θ. In some embodiments, provided herein is a solid form comprising pomalidomide and gallic acid having an XRPD pattern comprising peaks at approximately 18.42, 26.16, and 26.90 degrees 2θ. In some embodiments, provided herein is a solid form comprising pomalidomide and gallic acid having an XRPD pattern comprising peaks at approximately 23.20, 26.16, and 26.90 degrees 2θ.

In some embodiments, the XRPD peaks above (degrees 2θ peaks) are when analyzed using copper Kα radiation. In some embodiments, provided herein is a solid form comprising pomalidomide and gallic acid, wherein the solid form is characterized by an XRPD diffraction pattern which matches the XRPD pattern presented in FIG. 1.

5.2.2 Cocrystal Comprising Pomalidomide and Vanillin

Certain embodiments herein provide solid forms comprising pomalidomide and vanillin. In one embodiment, provided herein is a solid form comprising pomalidomide and vanillin that is substantially crystalline. In one embodiment, provided herein is a cocrystal comprising pomalidomide and vanillin. In one embodiment, provided herein is a solid form comprising a cocrystal comprising pomalidomide and vanillin. In one embodiment, provided herein is a solid form comprising (i) a cocrystal comprising pomalidomide and vanillin and (ii) an amorphous form of pomalidomide. In one embodiment, provided herein is a solid form comprising (i) a cocrystal comprising pomalidomide and vanillin and (ii) one or more additional crystal forms of pomalidomide. Provided herein are various embodiments, preparations, or modifications of a cocrystal comprising pomalidomide and vanillin.

In some embodiments, the cocrystal comprising pomalidomide and vanillin is obtained by grinding pomalidomide and vanillin together in the presence of a minor quantity of a solvent system. In some embodiments, the cocrystal comprising pomalidomide and vanillin is obtained by grinding approximately equal molar amount of pomalidomide and vanillin together in the presence of a minor quantity of a solvent system. In some embodiments, the solvent system is acetone.

In some embodiments, the cocrystal comprising pomalidomide and vanillin is obtained by removing solvent from a solution containing pomalidomide and vanillin. In some embodiments, the cocrystal is obtained by removing solvent from a solution containing pomalidomide and vanillin on a rotary evaporator at about 65° C. In some embodiments, the cocrystal is obtained by removing solvent from a solution containing pomalidomide and vanillin, and subsequently storing the residue at about 75% relative humidity for 1 day. In some embodiments, the cocrystal is obtained by removing solvent from a solution containing pomalidomide and vanillin, and subsequently storing the residue at about 60° C. overnight. In some embodiments, the cocrystal is obtained by removing solvent from a solution containing approximately equal molar amount of pomalidomide and vanillin. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and vanillin with a molar ratio of pomalidomide to vanillin of approximately 2:1 to 1:2. In some embodiments, the molar ratio of pomalidomide to vanillin is approximately 1:1.

A representative XRPD pattern of a solid form comprising pomalidomide and vanillin is provided in FIG. 2. In some embodiments, provided herein is a solid form comprising pomalidomide and vanillin characterized by one or more XRPD peaks (e.g., 1, 2, 3, 4, 5, 6, 7, 8, 9, 10, 11, 12, 13, 14, 15, 16, 17, 18, 19, 20, 21, or more peaks) selected from peaks located at the following or approximately the following positions: 11.68, 12.25, 12.73, 13.09, 14.02, 14.45, 15.44, 16.22, 16.91, 17.30, 18.40, 19.22, 20.04, 21.10, 21.58, 21.76, 22.63, 22.95, 23.53, 23.87, 24.33, 24.85, 25.61, 25.96, 26.66, 26.89, 28.01, 29.35, 31.96, 32.91, 33.91, 34.93, and 35.65 degrees 2θ, plus or minus 0.10. In some embodiments, provided herein is a solid form comprising pomalidomide and vanillin characterized by one or more XRPD peaks (e.g., 1, 2, 3, 4, 5, 6, 7, 8, 9, 10, 11, 12, 13, 14, 15, 16, 17, 18, 19, 20, 21, or more peaks) selected from peaks located at the following or approximately the following positions: 11.68, 12.25, 12.73, 13.09, 14.02, 15.44, 16.22, 16.91, 17.30, 18.40, 22.95, 24.33, 24.85, 25.61, 25.96, 26.66, 26.89, 28.01, 29.35, 31.96, and 33.91 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and vanillin having an XRPD pattern comprising peaks at approximately 13.09, 17.30, and 25.61 degrees 2θ. In certain embodiments, the solid form further comprises peaks at approximately 12.25, 16.91, and 28.01 degrees 2θ. In one embodiment, the solid form comprises peaks at approximately 11.68, 12.25, 12.73, 13.09, 14.02, 15.44, 16.22, 16.91, 17.30, 18.40, 22.95, 24.33, 24.85, 25.61, 25.96, 26.66, 26.89, 28.01, 29.35, 31.96, and 33.91 degrees 2θ.

In some embodiments, provided herein is a solid form comprising pomalidomide and vanillin having an XRPD pattern comprising peaks at approximately 13.09, 12.25, and 25.61 degrees 2θ. In some embodiments, provided herein is a solid form comprising pomalidomide and vanillin having an XRPD pattern comprising peaks at approximately 13.09, 16.91, and 25.61 degrees 2θ. In some embodiments, provided herein is a solid form comprising pomalidomide and vanillin having an XRPD pattern comprising peaks at approximately 13.09, 28.01, and 25.61 degrees 2θ.

In some embodiments, the XRPD peaks above (degrees 2θ peaks) are when analyzed using copper Kα radiation. In some embodiments, provided herein is a solid form comprising pomalidomide and vanillin, wherein the solid form is characterized by an XRPD diffraction pattern which matches the XRPD pattern presented in FIG. 2.

5.2.3 Cocrystal Comprising Pomalidomide and Cyclamic Acid

Certain embodiments herein provide solid forms comprising pomalidomide and cyclamic acid. In one embodiment, provided herein is a solid form comprising pomalidomide and cyclamic acid that is substantially crystalline. In one embodiment, provided herein is a cocrystal comprising pomalidomide and cyclamic acid. In one embodiment, provided herein is a solid form comprising a cocrystal comprising pomalidomide and cyclamic acid. In one embodiment, provided herein is a solid form comprising (i) a cocrystal comprising pomalidomide and cyclamic acid and (ii) an amorphous form of pomalidomide. In one embodiment, provided herein is a solid form comprising (i) a cocrystal comprising pomalidomide and cyclamic acid and (ii) one or more additional crystal forms of pomalidomide. Provided herein are various embodiments, preparations, or modifications of a cocrystal comprising pomalidomide and cyclamic acid.

In some embodiments, the cocrystal comprising pomalidomide and cyclamic acid is obtained by mixing pomalidomide and cyclamic acid in a solvent system. In some embodiments, the cocrystal is obtained by mixing pomalidomide and cyclamic acid in a solvent system saturated with cyclamic acid. In some embodiments, the cocrystal is obtained by mixing pomalidomide and cyclamic acid in a solvent system saturated with cyclamic acid, and subsequently stirring the mixture at room temperature for about 24 hours. In some embodiments, the cocrystal is obtained by mixing pomalidomide and cyclamic acid in a solvent system saturated with cyclamic acid, subsequently stirring the mixture at room temperature for about 24 hours, and isolating the solid by centrifugation. In some embodiments, the cocrystal is obtained by mixing approximately equal molar amount of pomalidomide and cyclamic acid in a solvent system saturated with cyclamic acid. In some embodiments, the solvent system is a mixed solvent of DMF and acetone with a volumn ratio of DMF to acetone of about 1:2.

In some embodiments, provided herein is a cocrystal comprising pomalidomide and cyclamic acid with a molar ratio of pomalidomide to cyclamic acid of approximately 2:1 to 1:2. In some embodiments, the molar ratio of pomalidomide to cyclamic acid is approximately 1:1.

A representative XRPD pattern of a solid form comprising pomalidomide and cyclamic acid is provided in FIG. 3. In some embodiments, provided herein is a solid form comprising pomalidomide and cyclamic acid characterized by one or more XRPD peaks (e.g., 1, 2, 3, 4, 5, 6, 7, 8, 9, 10, or more peaks) selected from peaks located at the following or approximately the following positions: 5.78, 6.42, 7.10, 7.88, 12.18, 12.81, 14.03, 15.73, 16.23, 17.31, 18.30, 18.54, 18.66, 19.25, 20.26, 21.27, 21.66, 23.69, 24.45, 25.49, 26.00, 26.80, 27.72, 28.08, 28.64, 30.30, 31.18, 32.32, 33.16, 34.93, 37.07, 37.47, and 39.02 degrees 2θ, plus or minus 0.10. In some embodiments, provided herein is a solid form comprising pomalidomide and cyclamic acid characterized by one or more XRPD peaks (e.g., 1, 2, 3, 4, 5, 6, 7, 8, 9, 10, or more peaks) selected from peaks located at the following or approximately the following positions: 6.42, 7.88, 15.73, 18.30, 18.54, 19.25, 21.27, 21.66, 25.49, and 33.16 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising pomalidomide and cyclamic acid having an XRPD pattern comprising peaks at approximately 6.42 and 7.88 degrees 2θ. In some embodiments, provided herein is a solid form comprising pomalidomide and cyclamic acid having an XRPD pattern comprising peaks at approximately 6.42, 7.88, and 15.73 degrees 2θ. In certain embodiments, the solid form further comprises peaks at approximately 18.54 and 19.25 degrees 2θ. In one embodiment, the solid form comprises peaks at approximately 6.42, 7.88, 15.73, 18.30, 18.54, 19.25, 21.27, 21.66, 25.49, and 33.16 degrees 2θ.

In some embodiments, provided herein is a solid form comprising pomalidomide and cyclamic acid having an XRPD pattern comprising peaks at approximately 6.42, 7.88, and 18.54 degrees 2θ. In some embodiments, provided herein is a solid form comprising pomalidomide and cyclamic acid having an XRPD pattern comprising peaks at approximately 6.42, 7.88, and 19.25 degrees 2θ.

In some embodiments, the XRPD peaks above (degrees 2θ peaks) are when analyzed using copper Kα radiation. In some embodiments, provided herein is a solid form comprising pomalidomide and cyclamic acid, wherein the solid form is characterized by an XRPD diffraction pattern which matches the XRPD pattern presented in FIG. 3.

5.2.4 Cocrystal Comprising Pomalidomide and D-Glucose

Certain embodiments herein provide solid forms comprising pomalidomide and D-glucose. In one embodiment, provided herein is a solid form comprising pomalidomide and D-glucose that is substantially crystalline. In one embodiment, provided herein is a cocrystal comprising pomalidomide and D-glucose. In one embodiment, provided herein is a solid form comprising a cocrystal comprising pomalidomide and D-glucose. In one embodiment, provided herein is a solid form comprising (i) a cocrystal comprising pomalidomide and D-glucose and (ii) an amorphous form of pomalidomide. In one embodiment, provided herein is a solid form comprising (i) a cocrystal comprising pomalidomide and D-glucose and (ii) one or more additional crystal forms of pomalidomide. Provided herein are various embodiments, preparations, or modifications of a cocrystal comprising pomalidomide and D-glucose.

In some embodiments, the cocrystal comprising pomalidomide and D-glucose is obtained by mixing pomalidomide and D-glucose in a solvent system. In some embodiments, the cocrystal is obtained by mixing pomalidomide and D-glucose in a solvent system saturated with D-glucose. In some embodiments, the cocrystal is obtained by mixing pomalidomide and D-glucose in a solvent system saturated with D-glucose, and subsequently stirring the mixture at room temperature for about 24 hours. In some embodiments, the cocrystal is obtained by mixing pomalidomide and D-glucose in a solvent system saturated with D-glucose, subsequently stirring the mixture at room temperature for about 24 hours, and isolating the solid by centrifugation. In some embodiments, the cocrystal is obtained by mixing approximately equal molar amount of pomalidomide and D-glucose in a solvent system saturated with D-glucose. In some embodiments, the solvent system is a mixed solvent of DMF and methanol with a volumn ratio of DMF to methanol of about 1:1.

In some embodiments, provided herein is a cocrystal comprising pomalidomide and D-glucose with a molar ratio of pomalidomide to D-glucose of approximately 2:1 to 1:2. In some embodiments, the molar ratio of pomalidomide to D-glucose is approximately 1:1.

A representative XRPD pattern of a solid form comprising pomalidomide and D-glucose is provided in FIG. 4. In some embodiments, provided herein is a solid form comprising pomalidomide and D-glucose characterized by one or more XRPD peaks (e.g., 1, 2, 3, 4, 5, 6, 7, 8, 9, 10, 11, 12, 13, 14, or more peaks) selected from peaks located at the following or approximately the following positions: 5.27, 10.44, 11.84, 12.31, 12.72, 14.08, 14.70, 16.18, 16.54, 17.09, 17.35, 18.43, 18.80, 19.31, 19.76, 20.20, 20.68, 22.85, 23.13, 24.31, 24.79, 25.52, 26.81, 27.57, 28.00, 28.47, 29.20, 30.01, 30.72, 31.29, 31.65, 32.05, 33.92, 34.60, 34.75, 35.14, 36.06, 36.26, 36.56, 37.60, 39.14, 39.34, 39.62, and 39.95 degrees 2θ, plus or minus 0.10. In some embodiments, provided herein is a solid form comprising pomalidomide and D-glucose characterized by one or more XRPD peaks (e.g., 1, 2, 3, 4, 5, 6, 7, 8, 9, 10, 11, 12, 13, 14, or more peaks) selected from peaks located at the following or approximately the following positions: 11.84, 12.31, 14.08, 17.09, 17.35, 18.43, 18.80, 20.68, 24.31, 24.79, 25.52, 28.00, 28.47, and 29.20 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising pomalidomide and D-glucose having an XRPD pattern comprising peaks at approximately 17.09, 20.68, and 25.52 degrees 2θ. In certain embodiments, the solid form further comprises peaks at approximately 12.31, 14.08, and 17.35 degrees 2θ. In one embodiment, the solid form comprises peaks at approximately 11.84, 12.31, 14.08, 17.09, 17.35, 18.43, 18.80, 20.68, 24.31, 24.79, 25.52, 28.00, 28.47, and 29.20 degrees 2θ.

In some embodiments, provided herein is a solid form comprising pomalidomide and D-glucose having an XRPD pattern comprising peaks at approximately 12.31, 20.68, and 25.52 degrees 2θ. In some embodiments, provided herein is a solid form comprising pomalidomide and D-glucose having an XRPD pattern comprising peaks at approximately 14.08, 20.68, and 25.52 degrees 2θ. In some embodiments, provided herein is a solid form comprising pomalidomide and D-glucose having an XRPD pattern comprising peaks at approximately 17.35, 20.68, and 25.52 degrees 2θ.

In some embodiments, the XRPD peaks above (degrees 2θ peaks) are when analyzed using copper Kα radiation. In some embodiments, provided herein is a solid form comprising pomalidomide and D-glucose, wherein the solid form is characterized by an XRPD diffraction pattern which matches the XRPD pattern presented in FIG. 4.

5.2.5 Cocrystal Comprising Pomalidomide and Propyl Gallate

Certain embodiments herein provide solid forms comprising pomalidomide and propyl gallate. In one embodiment, provided herein is a solid form comprising pomalidomide and propyl gallate that is substantially crystalline. In one embodiment, provided herein is a cocrystal comprising pomalidomide and propyl gallate. In one embodiment, provided herein is a solid form comprising a cocrystal comprising pomalidomide and propyl gallate. In one embodiment, provided herein is a solid form comprising (i) a cocrystal comprising pomalidomide and propyl gallate and (ii) an amorphous form of pomalidomide. In one embodiment, provided herein is a solid form comprising (i) a cocrystal comprising pomalidomide and propyl gallate and (ii) one or more additional crystal forms of pomalidomide. Provided herein are various embodiments, preparations, or modifications of a cocrystal comprising pomalidomide and propyl gallate.

In some embodiments, the cocrystal comprising pomalidomide and propyl gallate is obtained by mixing pomalidomide and propyl gallate in a solvent system. In some embodiments, the cocrystal is obtained by mixing pomalidomide and propyl gallate in a solvent system saturated with propyl gallate. In some embodiments, the cocrystal is obtained by mixing pomalidomide and propyl gallate in a solvent system saturated with propyl gallate, and subsequently stirring the mixture at room temperature for about 24 hours. In some embodiments, the cocrystal is obtained by mixing pomalidomide and propyl gallate in a solvent system saturated with propyl gallate, subsequently stirring the mixture at room temperature for about 24 hours, and isolating the solid by centrifugation. In some embodiments, the cocrystal is obtained by mixing approximately equal molar amount of pomalidomide and propyl gallate in a solvent system saturated with propyl gallate. In some embodiments, the solvent system is a mixed solvent of DMF and methanol with a volumn ratio of DMF to methanol of about 1:1.

In some embodiments, provided herein is a cocrystal comprising pomalidomide and propyl gallate with a molar ratio of pomalidomide to propyl gallate of approximately 2:1 to 1:2. In some embodiments, the molar ratio of pomalidomide to propyl gallate is approximately 1:1.

A representative XRPD pattern of a solid form comprising pomalidomide and propyl gallate is provided in FIG. 5. In some embodiments, provided herein is a solid form comprising pomalidomide and propyl gallate characterized by one or more XRPD peaks (e.g., 1, 2, 3, 4, 5, 6, 7, 8, 9, 10, 11, 12, 13, or more peaks) selected from peaks located at the following or approximately the following positions: 4.88, 7.23, 7.78, 8.87, 9.46, 11.36, 11.75, 12.29, 12.76, 13.30, 14.08, 15.52, 16.19, 16.54, 16.97, 17.03, 17.35, 18.25, 18.42, 18.90, 19.35, 19.80, 22.89, 23.33, 24.29, 25.23, 25.61, 27.71, 28.02, 28.39, 29.26, 32.17, 33.95, and 35.80 degrees 2θ, plus or minus 0.10. In some embodiments, provided herein is a solid form comprising pomalidomide and propyl gallate characterized by one or more XRPD peaks (e.g., 1, 2, 3, 4, 5, 6, 7, 8, 9, 10, 11, 12, 13, or more peaks) selected from peaks located at the following or approximately the following positions: 7.78, 12.29, 12.76, 14.08, 16.97, 17.35, 18.42, 24.29, 25.23, 25.61, 28.02, 29.26, and 32.17 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising pomalidomide and propyl gallate having an XRPD pattern comprising peaks at approximately 7.78, 25.23, and 25.61 degrees 2θ. In certain embodiments, the solid form further comprises peaks at approximately 17.35 and 24.29 degrees 2θ. In certain embodiments, the solid form further comprises peaks at approximately 12.29 and 14.08 degrees 2θ. In one embodiment, the solid form comprises peaks at approximately 7.78, 12.29, 12.76, 14.08, 16.97, 17.35, 18.42, 24.29, 25.23, 25.61, 28.02, 29.26, and 32.17 degrees 2θ.

In some embodiments, provided herein is a solid form comprising pomalidomide and propyl gallate having an XRPD pattern comprising peaks at approximately 7.78, 12.29, 25.23, and 25.61 degrees 2θ. In some embodiments, provided herein is a solid form comprising pomalidomide and propyl gallate having an XRPD pattern comprising peaks at approximately 7.78, 14.08, 25.23, and 25.61 degrees 2θ. In some embodiments, provided herein is a solid form comprising pomalidomide and propyl gallate having an XRPD pattern comprising peaks at approximately 7.78, 17.35, 25.23, and 25.61 degrees 2θ. In some embodiments, provided herein is a solid form comprising pomalidomide and propyl gallate having an XRPD pattern comprising peaks at approximately 7.78, 24.29, 25.23, and 25.61 degrees 2θ.

In some embodiments, the XRPD peaks above (degrees 2θ peaks) are when analyzed using copper Kα radiation. In some embodiments, provided herein is a solid form comprising pomalidomide and propyl gallate, wherein the solid form is characterized by an XRPD diffraction pattern which matches the XRPD pattern presented in FIG. 5.

5.2.6 Cocrystal Comprising Pomalidomide and Saccharin

Certain embodiments herein provide solid forms comprising pomalidomide and saccharin. In one embodiment, provided herein is a solid form comprising pomalidomide and saccharin that is substantially crystalline. In one embodiment, provided herein is a cocrystal comprising pomalidomide and saccharin. In one embodiment, provided herein is a solid form comprising a cocrystal comprising pomalidomide and saccharin. In one embodiment, provided herein is a solid form comprising (i) a cocrystal comprising pomalidomide and saccharin and (ii) an amorphous form of pomalidomide. In one embodiment, provided herein is a solid form comprising (i) a cocrystal comprising pomalidomide and saccharin and (ii) one or more additional crystal forms of pomalidomide. Provided herein are various embodiments, preparations, or modifications of a cocrystal comprising pomalidomide and saccharin.

In some embodiments, the cocrystal comprising pomalidomide and saccharin is obtained by mixing pomalidomide and saccharin in a solvent system. In some embodiments, the cocrystal is obtained by mixing pomalidomide and saccharin in a solvent system saturated with saccharin. In some embodiments, the cocrystal is obtained by mixing pomalidomide and saccharin in a solvent system saturated with saccharin, and subsequently stirring the mixture at room temperature for about 24 hours. In some embodiments, the cocrystal is obtained by mixing pomalidomide and saccharin in a solvent system saturated with saccharin, subsequently stirring the mixture at room temperature for about 24 hours, and isolating the solid by centrifugation. In some embodiments, the cocrystal is obtained by mixing approximately equal molar amount of pomalidomide and saccharin in a solvent system saturated with saccharin. In some embodiments, the solvent system is a mixed solvent of DMF and methanol with a volumn ratio of DMF to methanol of about 1:1.

In some embodiments, provided herein is a cocrystal comprising pomalidomide and saccharin with a molar ratio of pomalidomide to saccharin of approximately 2:1 to 1:2. In some embodiments, the molar ratio of pomalidomide to saccharin is approximately 1:1.

A representative XRPD pattern of a solid form comprising pomalidomide and saccharin is provided in FIG. 6. In some embodiments, provided herein is a solid form comprising pomalidomide and saccharin characterized by one or more XRPD peaks (e.g., 1, 2, 3, 4, 5, 6, 7, 8, 9, 10, 11, 12, 13, 14, 15, 16, 17, or more peaks) selected from peaks located at the following or approximately the following positions: 8.52, 9.53, 11.75, 12.31, 12.71, 13.48, 14.07, 14.91, 15.39, 15.98, 16.50, 16.94, 17.36, 18.44, 19.09, 20.07, 21.51, 22.80, 23.61, 23.80, 24.33, 24.99, 25.10, 25.53, 25.73, 26.24, 27.38, 27.95, 28.44, 28.80, 29.15, 29.38, 30.48, 30.83, 32.02, 32.28, 33.72, 34.27, 34.97, 37.90, and 38.33 degrees 2θ, plus or minus 0.10. In some embodiments, provided herein is a solid form comprising pomalidomide and saccharin characterized by one or more XRPD peaks (e.g., 1, 2, 3, 4, 5, 6, 7, 8, 9, 10, 11, 12, 13, 14, 15, 16, 17, or more peaks) selected from peaks located at the following or approximately the following positions: 12.31, 13.48, 14.07, 15.98, 16.94, 17.36, 18.44, 19.09, 20.07, 22.80, 23.80, 24.33, 25.10, 25.53, 25.73, 27.38, and 27.95 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and saccharin having an XRPD pattern comprising peaks at approximately 15.98, 19.09, and 25.10 degrees 2θ. In certain embodiments, the solid form further comprises peaks at approximately 20.07 and 25.73 degrees 2θ. In certain embodiments, the solid form further comprises peaks at approximately 17.36 and 25.53 degrees 2θ. In one embodiment, the solid form comprises peaks at approximately 12.31, 13.48, 14.07, 15.98, 16.94, 17.36, 18.44, 19.09, 20.07, 22.80, 23.80, 24.33, 25.10, 25.53, 25.73, 27.38, and 27.95 degrees 2θ.

In some embodiments, provided herein is a solid form comprising pomalidomide and saccharin having an XRPD pattern comprising peaks at approximately 15.98, 17.36, and 25.10 degrees 2θ. In some embodiments, provided herein is a solid form comprising pomalidomide and saccharin having an XRPD pattern comprising peaks at approximately 15.98, 20.07, and 25.10 degrees 2θ. In some embodiments, provided herein is a solid form comprising pomalidomide and saccharin having an XRPD pattern comprising peaks at approximately 15.98, 25.10, and 25.53 degrees 2θ. In some embodiments, provided herein is a solid form comprising pomalidomide and saccharin having an XRPD pattern comprising peaks at approximately 15.98, 25.10, and 25.73 degrees 2θ.

In some embodiments, the XRPD peaks above (degrees 2θ peaks) are when analyzed using copper Kα radiation. In some embodiments, provided herein is a solid form comprising pomalidomide and saccharin, wherein the solid form is characterized by an XRPD diffraction pattern which matches the XRPD pattern presented in FIG. 6.

5.2.7 Cocrystal Comprising Pomalidomide and Sodium Lauryl Sulfate

Certain embodiments herein provide solid forms comprising pomalidomide and sodium lauryl sulfate. In one embodiment, provided herein is a solid form comprising pomalidomide and sodium lauryl sulfate that is substantially crystalline. In one embodiment, provided herein is a cocrystal comprising pomalidomide and sodium lauryl sulfate. In one embodiment, provided herein is a solid form comprising a cocrystal comprising pomalidomide and sodium lauryl sulfate. In one embodiment, provided herein is a solid form comprising (i) a cocrystal comprising pomalidomide and sodium lauryl sulfate and (ii) an amorphous form of pomalidomide. In one embodiment, provided herein is a solid form comprising (i) a cocrystal comprising pomalidomide and sodium lauryl sulfate and (ii) one or more additional crystal forms of pomalidomide. Provided herein are various embodiments, preparations, or modifications of a cocrystal comprising pomalidomide and sodium lauryl sulfate.

In some embodiments, the cocrystal comprising pomalidomide and sodium lauryl sulfate is obtained by grinding pomalidomide and sodium lauryl sulfate together in the presence of a minor quantity of a solvent system. In some embodiments, the cocrystal comprising pomalidomide and sodium lauryl sulfate is obtained by grinding approximately equal molar amount of pomalidomide and sodium lauryl sulfate together in the presence of a minor quantity of a solvent system. In some embodiments, the solvent system is a mixed solvent of acetone and methanol. In one embodiment, the solvent system is a mixed solvent of acetone and methanol with a volumn ratio of acetone to methanol of about 1:1.

In some embodiments, provided herein is a cocrystal comprising pomalidomide and sodium lauryl sulfate with a molar ratio of pomalidomide to sodium lauryl sulfate of approximately 2:1 to 1:2. In some embodiments, the molar ratio of pomalidomide to sodium lauryl sulfate is approximately 1:1.

A representative XRPD pattern of a solid form comprising pomalidomide and sodium lauryl sulfate is provided in FIG. 7. In some embodiments, provided herein is a solid form comprising pomalidomide and sodium lauryl sulfate characterized by one or more XRPD peaks (e.g., 1, 2, 3, 4, 5, 6, 7, 8, 9, 10, 11, 12, 13, 14, 15, 16, 17, 18, 19, or more peaks) selected from peaks located at the following or approximately the following positions: 2.20, 2.66, 4.36, 5.30, 6.53, 7.93, 10.62, 12.20, 12.68, 13.26, 14.00, 16.16, 16.90, 17.27, 18.35, 20.37, 20.66, 20.98, 21.42, 21.71, 22.86, 24.29, 24.75, 25.53, 26.72, 27.98, 29.19, 32.07, and 33.88 degrees 2θ, plus or minus 0.10. In some embodiments, provided herein is a solid form comprising pomalidomide and sodium lauryl sulfate characterized by one or more XRPD peaks (e.g., 1, 2, 3, 4, 5, 6, 7, 8, 9, 10, 11, 12, 13, 14, 15, 16, 17, 18, 19, or more peaks) selected from peaks located at the following or approximately the following positions: 2.20, 2.66, 4.36, 5.30, 7.93, 10.62, 12.20, 13.26, 14.00, 16.90, 17.27, 18.35, 20.66, 21.42, 24.29, 24.75, 25.53, 27.98, and 29.19 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and sodium lauryl sulfate having an XRPD pattern comprising peaks at approximately 2.66, 5.30, and 7.93 degrees 2θ. In certain embodiments, the solid form further comprises a peak at approximately 2.20 degrees 2θ. In certain embodiments, the solid form further comprises peaks at approximately 12.20, 17.27, and 25.53 degrees 2θ. In one embodiment, the solid form comprises peaks at approximately 2.20, 2.66, 4.36, 5.30, 7.93, 10.62, 12.20, 13.26, 14.00, 16.90, 17.27, 18.35, 20.66, 21.42, 24.29, 24.75, 25.53, 27.98, and 29.19 degrees 2θ.

In some embodiments, the XRPD peaks above (degrees 2θ peaks) are when analyzed using copper Kα radiation. In some embodiments, provided herein is a solid form comprising pomalidomide and sodium lauryl sulfate, wherein the solid form is characterized by an XRPD diffraction pattern which matches the XRPD pattern presented in FIG. 7.

5.2.8 Cocrystal Comprising Pomalidomide and Magnesium Bromide

Certain embodiments herein provide solid forms comprising pomalidomide and magnesium bromide. In one embodiment, provided herein is a solid form comprising pomalidomide and magnesium bromide that is substantially crystalline. In one embodiment, provided herein is a cocrystal comprising pomalidomide and magnesium bromide. In one embodiment, provided herein is a solid form comprising a cocrystal comprising pomalidomide and magnesium bromide. In one embodiment, provided herein is a solid form comprising (i) a cocrystal comprising pomalidomide and magnesium bromide and (ii) an amorphous form of pomalidomide. In one embodiment, provided herein is a solid form comprising (i) a cocrystal comprising pomalidomide and magnesium bromide and (ii) one or more additional crystal forms of pomalidomide. Provided herein are various embodiments, preparations, or modifications of a cocrystal comprising pomalidomide and magnesium bromide.

In some embodiments, the cocrystal comprising pomalidomide and magnesium bromide is obtained by removing solvent from a solution containing pomalidomide and magnesium bromide. In some embodiments, the cocrystal is obtained by removing solvent from a solution containing pomalidomide and magnesium bromide on a rotary evaporator at about 65° C. In some embodiments, the cocrystal is obtained by removing solvent from a solution containing pomalidomide and magnesium bromide, and subsequently storing the residue at about 75% relative humidity for 1 day. In some embodiments, the cocrystal is obtained by removing solvent from a solution containing pomalidomide and magnesium bromide, and subsequently storing the residue at about 60° C. overnight. In some embodiments, the cocrystal is obtained by removing solvent from a solution containing approximately equal molar amount of pomalidomide and magnesium bromide. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and magnesium bromide with a molar ratio of pomalidomide to magnesium bromide of approximately 2:1 to 1:2. In some embodiments, the molar ratio of pomalidomide to magnesium bromide is approximately 1:1.

A representative XRPD pattern of a solid form comprising pomalidomide and magnesium bromide is provided in FIG. 8. In some embodiments, provided herein is a solid form comprising pomalidomide and magnesium bromide characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 3.23, 11.91, 12.79, 13.95, 14.74, 16.21, 16.60, 17.16, 18.38, 20.10, 24.28, 24.80, 25.72, 28.58, 28.76, 29.87, 29.95, 32.08, and 32.79 degrees 2θ, plus or minus 0.10. In some embodiments, provided herein is a solid form comprising pomalidomide and magnesium bromide characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 3.23, 11.91, 13.95, 14.74, 16.60, 17.16, 18.38, 20.10, 24.28, 24.80, 25.72, 28.58, 28.76, 29.87, 29.95, and 32.79 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and magnesium bromide having an XRPD pattern comprising peaks at approximately 3.23, 28.76, and 29.95 degrees 2θ. In certain embodiments, the solid form further comprises peaks at approximately 25.72 and 29.87 degrees 2θ. In certain embodiments, the solid form further comprises peaks at approximately 17.16 and 28.58 degrees 2θ. In one embodiment, the solid form comprises peaks at approximately 3.23, 11.91, 13.95, 14.74, 16.60, 17.16, 18.38, 20.10, 24.28, 24.80, 25.72, 28.58, 28.76, 29.87, 29.95, and 32.79 degrees 2θ.

In some embodiments, provided herein is a solid form comprising pomalidomide and magnesium bromide having an XRPD pattern comprising peaks at approximately 17.16, 28.76, and 29.95 degrees 2θ. In some embodiments, provided herein is a solid form comprising pomalidomide and magnesium bromide having an XRPD pattern comprising peaks at approximately 25.72, 28.76, and 29.95 degrees 2θ. In some embodiments, provided herein is a solid form comprising pomalidomide and magnesium bromide having an XRPD pattern comprising peaks at approximately 28.58, 28.76, and 29.95 degrees 2θ. In some embodiments, provided herein is a solid form comprising pomalidomide and magnesium bromide having an XRPD pattern comprising peaks at approximately 28.76, 29.87, and 29.95 degrees 2θ.

In some embodiments, the XRPD peaks above (degrees 2θ peaks) are when analyzed using copper Kα radiation. In some embodiments, provided herein is a solid form comprising pomalidomide and magnesium bromide, wherein the solid form is characterized by an XRPD diffraction pattern which matches the XRPD pattern presented in FIG. 8.

5.2.9 Cocrystal Comprising Pomalidomide and Malonic Acid

Certain embodiments herein provide solid forms comprising pomalidomide and malonic acid. In one embodiment, provided herein is a solid form comprising pomalidomide and malonic acid that is substantially crystalline. In one embodiment, provided herein is a cocrystal comprising pomalidomide and malonic acid. In one embodiment, provided herein is a solid form comprising a cocrystal comprising pomalidomide and malonic acid. In one embodiment, provided herein is a solid form comprising (i) a cocrystal comprising pomalidomide and malonic acid and (ii) an amorphous form of pomalidomide. In one embodiment, provided herein is a solid form comprising (i) a cocrystal comprising pomalidomide and malonic acid and (ii) one or more additional crystal forms of pomalidomide. Provided herein are various embodiments, preparations, or modifications of a cocrystal comprising pomalidomide and malonic acid.

In some embodiments, the cocrystal comprising pomalidomide and malonic acid is obtained by removing solvent from a solution containing pomalidomide and malonic acid. In some embodiments, the cocrystal is obtained by removing solvent from a solution containing pomalidomide and malonic acid on a rotary evaporator at about 65° C. In some embodiments, the cocrystal is obtained by removing solvent from a solution containing pomalidomide and malonic acid, and subsequently storing the residue at about 75% relative humidity for 1 day. In some embodiments, the cocrystal is obtained by removing solvent from a solution containing pomalidomide and malonic acid, and subsequently storing the residue at about 60° C. overnight. In some embodiments, the cocrystal is obtained by removing solvent from a solution containing approximately equal molar amount of pomalidomide and malonic acid. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and malonic acid with a molar ratio of pomalidomide to malonic acid of approximately 2:1 to 1:2. In some embodiments, the molar ratio of pomalidomide to malonic acid is approximately 1:1.

A representative XRPD pattern of a solid form comprising pomalidomide and malonic acid is provided in FIG. 9. In some embodiments, provided herein is a solid form comprising pomalidomide and malonic acid characterized by one or more XRPD peaks (e.g., 1, 2, 3, 4, 5, 6, 7, 8, 9, 10, 11, 12, 13, 14, 15, 16, 17, 18, 19, 20, 21, or more peaks) selected from peaks located at the following or approximately the following positions: 12.23, 12.73, 13.99, 16.18, 16.63, 17.27, 18.37, 18.81, 19.18, 20.42, 21.83, 22.44, 23.34, 23.79, 24.29, 24.85, 25.58, 27.98, 28.44, 29.33, 30.96, 31.34, 32.58, 33.08, 33.90, 35.28, 37.36, 38.08, 38.59, and 39.43 degrees 2θ, plus or minus 0.10. In some embodiments, provided herein is a solid form comprising pomalidomide and malonic acid characterized by one or more XRPD peaks (e.g., 1, 2, 3, 4, 5, 6, 7, 8, 9, 10, 11, 12, 13, 14, 15, 16, 17, 18, 19, 20, 21, or more peaks) selected from peaks located at the following or approximately the following positions: 12.23, 12.73, 13.99, 16.18, 16.63, 17.27, 18.37, 21.83, 22.44, 23.34, 23.79, 24.29, 24.85, 25.58, 27.98, 28.44, 29.33, 30.96, 32.58, 33.90, and 37.36 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and malonic acid having an XRPD pattern comprising peaks at approximately 12.23, 16.63, and 25.58 degrees 2θ. In certain embodiments, the solid form further comprises peaks at approximately 17.27 and 24.29 degrees 2θ. In certain embodiments, the solid form further comprises peaks at approximately 13.99, 23.34, and 27.98 degrees 2θ. In one embodiment, the solid form comprises peaks at approximately 12.23, 12.73, 13.99, 16.18, 16.63, 17.27, 18.37, 21.83, 22.44, 23.34, 23.79, 24.29, 24.85, 25.58, 27.98, 28.44, 29.33, 30.96, 32.58, 33.90, and 37.36 degrees 2θ.

In some embodiments, provided herein is a solid form comprising pomalidomide and malonic acid having an XRPD pattern comprising peaks at approximately 13.99, 16.63, and 25.58 degrees 2θ. In some embodiments, provided herein is a solid form comprising pomalidomide and malonic acid having an XRPD pattern comprising peaks at approximately 16.63, 17.27, and 25.58 degrees 2θ. In some embodiments, provided herein is a solid form comprising pomalidomide and malonic acid having an XRPD pattern comprising peaks at approximately 16.63, 23.34, and 25.58 degrees 2θ. In some embodiments, provided herein is a solid form comprising pomalidomide and malonic acid having an XRPD pattern comprising peaks at approximately 16.63, 24.29, and 25.58 degrees 2θ. In some embodiments, provided herein is a solid form comprising pomalidomide and malonic acid having an XRPD pattern comprising peaks at approximately 16.63, 25.58, and 27.98 degrees 2θ.

In some embodiments, the XRPD peaks above (degrees 2θ peaks) are when analyzed using copper Kα radiation. In some embodiments, provided herein is a solid form comprising pomalidomide and malonic acid, wherein the solid form is characterized by an XRPD diffraction pattern which matches the XRPD pattern presented in FIG. 9.

5.2.10 Cocrystal Comprising Pomalidomide and Maltol

Certain embodiments herein provide solid forms comprising pomalidomide and maltol. In one embodiment, provided herein is a solid form comprising pomalidomide and maltol that is substantially crystalline. In one embodiment, provided herein is a cocrystal comprising pomalidomide and maltol. In one embodiment, provided herein is a solid form comprising a cocrystal comprising pomalidomide and maltol. In one embodiment, provided herein is a solid form comprising (i) a cocrystal comprising pomalidomide and maltol and (ii) an amorphous form of pomalidomide. In one embodiment, provided herein is a solid form comprising (i) a cocrystal comprising pomalidomide and maltol and (ii) one or more additional crystal forms of pomalidomide. Provided herein are various embodiments, preparations, or modifications of a cocrystal comprising pomalidomide and maltol.

In some embodiments, the cocrystal comprising pomalidomide and maltol is obtained by removing solvent from a solution containing pomalidomide and maltol. In some embodiments, the cocrystal is obtained by removing solvent from a solution containing pomalidomide and maltol on a rotary evaporator at about 65° C. In some embodiments, the cocrystal is obtained by removing solvent from a solution containing pomalidomide and maltol, and subsequently storing the residue at about 75% relative humidity for 1 day. In some embodiments, the cocrystal is obtained by removing solvent from a solution containing pomalidomide and maltol, and subsequently storing the residue at about 60° C. overnight. In some embodiments, the cocrystal is obtained by removing solvent from a solution containing approximately equal molar amount of pomalidomide and maltol. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and maltol with a molar ratio of pomalidomide to maltol of approximately 2:1 to 1:2. In some embodiments, the molar ratio of pomalidomide to maltol is approximately 1:1.

A representative XRPD pattern of a solid form comprising pomalidomide and maltol is provided in FIG. 10. In some embodiments, provided herein is a solid form comprising pomalidomide and maltol characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 11.41, 11.87, 12.75, 13.93, 14.54, 14.78, 16.51, 17.09, 18.34, 19.72, 22.98, 24.25, 24.74, 25.73, 26.33, 27.00, 27.91, 28.50, 29.46, 29.86, 30.17, 32.14, 33.17, 33.98, 34.97, and 35.66 degrees 2θ, plus or minus 0.10. In some embodiments, provided herein is a solid form comprising pomalidomide and maltol characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 11.87, 13.93, 14.54, 14.78, 16.51, 17.09, 18.34, 24.25, 24.74, 25.73, 26.33, 27.00, 27.91, 28.50, 29.46, and 32.14 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and maltol having an XRPD pattern comprising peaks at approximately 16.51, 17.09, and 25.73 degrees 2θ. In certain embodiments, the solid form further comprises peaks at approximately 13.93 and 24.25 degrees 2θ. In certain embodiments, the solid form further comprises peaks at approximately 11.87 and 14.54 degrees 2θ. In one embodiment, the solid form comprises peaks at approximately 11.87, 13.93, 14.54, 14.78, 16.51, 17.09, 18.34, 24.25, 24.74, 25.73, 26.33, 27.00, 27.91, 28.50, 29.46, and 32.14 degrees 2θ.

In some embodiments, provided herein is a solid form comprising pomalidomide and maltol having an XRPD pattern comprising peaks at approximately 11.87, 17.09, and 25.73 degrees 2θ. In some embodiments, provided herein is a solid form comprising pomalidomide and maltol having an XRPD pattern comprising peaks at approximately 13.93, 17.09, and 25.73 degrees 2θ. In some embodiments, provided herein is a solid form comprising pomalidomide and maltol having an XRPD pattern comprising peaks at approximately 14.54, 17.09, and 25.73 degrees 2θ. In some embodiments, provided herein is a solid form comprising pomalidomide and maltol having an XRPD pattern comprising peaks at approximately 17.09, 24.25, and 25.73 degrees 2θ.

In some embodiments, the XRPD peaks above (degrees 2θ peaks) are when analyzed using copper Kα radiation. In some embodiments, provided herein is a solid form comprising pomalidomide and maltol, wherein the solid form is characterized by an XRPD diffraction pattern which matches the XRPD pattern presented in FIG. 10.

5.2.11 Cocrystal Comprising Pomalidomide and Methyl Paraben

Certain embodiments herein provide solid forms comprising pomalidomide and methyl paraben. In one embodiment, provided herein is a solid form comprising pomalidomide and methyl paraben that is substantially crystalline. In one embodiment, provided herein is a cocrystal comprising pomalidomide and methyl paraben. In one embodiment, provided herein is a solid form comprising a cocrystal comprising pomalidomide and methyl paraben. In one embodiment, provided herein is a solid form comprising (i) a cocrystal comprising pomalidomide and methyl paraben and (ii) an amorphous form of pomalidomide. In one embodiment, provided herein is a solid form comprising (i) a cocrystal comprising pomalidomide and methyl paraben and (ii) one or more additional crystal forms of pomalidomide. Provided herein are various embodiments, preparations, or modifications of a cocrystal comprising pomalidomide and methyl paraben.

In some embodiments, the cocrystal comprising pomalidomide and methyl paraben is obtained by removing solvent from a solution containing pomalidomide and methyl paraben. In some embodiments, the cocrystal is obtained by removing solvent from a solution containing pomalidomide and methyl paraben on a rotary evaporator at about 65° C. In some embodiments, the cocrystal is obtained by removing solvent from a solution containing pomalidomide and methyl paraben, and subsequently storing the residue at about 75% relative humidity for 1 day. In some embodiments, the cocrystal is obtained by removing solvent from a solution containing pomalidomide and methyl paraben, and subsequently storing the residue at about 60° C. overnight. In some embodiments, the cocrystal is obtained by removing solvent from a solution containing approximately equal molar amount of pomalidomide and methyl paraben. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and methyl paraben with a molar ratio of pomalidomide to methyl paraben of approximately 2:1 to 1:2. In some embodiments, the molar ratio of pomalidomide to methyl paraben is approximately 1:1.

A representative XRPD pattern of a solid form comprising pomalidomide and methyl paraben is provided in FIG. 11. In some embodiments, provided herein is a solid form comprising pomalidomide and methyl paraben characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 10.46, 10.61, 11.38, 11.88, 12.70, 13.90, 14.71, 16.50, 17.10, 18.33, 18.73, 19.77, 21.00, 21.27, 21.75, 21.90, 21.98, 23.00, 23.95, 24.28, 24.38, 24.50, 25.69, 26.70, 27.85, 28.49, 29.01, 29.10, 30.14, 30.82, 32.10, 32.62, 33.09, 33.98, 34.77, and 36.87 degrees 2θ, plus or minus 0.10. In some embodiments, provided herein is a solid form comprising pomalidomide and methyl paraben characterized by one or more XRPD peaks (e.g., 1, 2, 3, 4, 5, 6, 7, 8, 9, 10, 11, 12, 13, 14, 15, 16, or more peaks) selected from peaks located at the following or approximately the following positions: 10.46, 10.61, 11.88, 13.90, 14.71, 16.50, 17.10, 18.33, 18.73, 19.77, 21.27, 21.98, 24.28, 24.38, 24.50, 25.69, 26.70, 28.49, and 29.01 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and methyl paraben having an XRPD pattern comprising peaks at approximately 18.73, 25.69, and 26.70 degrees 2θ. In certain embodiments, the solid form further comprises peaks at approximately 13.90 and 21.98 degrees 2θ. In certain embodiments, the solid form further comprises peaks at approximately 17.10, 24.38, and 29.01 degrees 2θ. In one embodiment, the solid form comprises peaks at approximately 10.46, 10.61, 11.88, 13.90, 14.71, 16.50, 17.10, 18.33, 18.73, 19.77, 21.27, 21.98, 24.28, 24.38, 24.50, 25.69, 26.70, 28.49, and 29.01 degrees 2θ.

In some embodiments, provided herein is a solid form comprising pomalidomide and methyl paraben having an XRPD pattern comprising peaks at approximately 18.73, 21.98, and 26.70 degrees 2θ. In some embodiments, provided herein is a solid form comprising pomalidomide and methyl paraben having an XRPD pattern comprising peaks at approximately 14.71, 21.98, and 26.70 degrees 2θ. In some embodiments, provided herein is a solid form comprising pomalidomide and methyl paraben having an XRPD pattern comprising peaks at approximately 21.98, 26.70, and 29.01 degrees 2θ.

In some embodiments, the XRPD peaks above (degrees 2θ peaks) are when analyzed using copper Kα radiation. In some embodiments, provided herein is a solid form comprising pomalidomide and methyl paraben, wherein the solid form is characterized by an XRPD diffraction pattern which matches the XRPD pattern presented in FIG. 11.

5.2.12 Cocrystal Comprising Pomalidomide and Zinc Chloride

Certain embodiments herein provide solid forms comprising pomalidomide and zinc chloride. In one embodiment, provided herein is a solid form comprising pomalidomide and zinc chloride that is substantially crystalline. In one embodiment, provided herein is a cocrystal comprising pomalidomide and zinc chloride. In one embodiment, provided herein is a solid form comprising a cocrystal comprising pomalidomide and zinc chloride. In one embodiment, provided herein is a solid form comprising (i) a cocrystal comprising pomalidomide and zinc chloride and (ii) an amorphous form of pomalidomide. In one embodiment, provided herein is a solid form comprising (i) a cocrystal comprising pomalidomide and zinc chloride and (ii) one or more additional crystal forms of pomalidomide. Provided herein are various embodiments, preparations, or modifications of a cocrystal comprising pomalidomide and zinc chloride.

In some embodiments, the cocrystal comprising pomalidomide and zinc chloride is obtained by removing solvent from a solution containing pomalidomide and zinc chloride. In some embodiments, the cocrystal is obtained by removing solvent from a solution containing pomalidomide and zinc chloride on a rotary evaporator at about 65° C. In some embodiments, the cocrystal is obtained by removing solvent from a solution containing pomalidomide and zinc chloride, and subsequently storing the residue at about 75% relative humidity for 1 day. In some embodiments, the cocrystal is obtained by removing solvent from a solution containing pomalidomide and zinc chloride, and subsequently storing the residue at about 60° C. overnight.

In some embodiments, the cocrystal is obtained by removing solvent from a solution containing approximately equal molar amount of pomalidomide and zinc chloride. In some embodiments, the solvent system is a mixed solvent of THF and water. In some embodiments, the solvent system is a mixed solvent of THF and water with a volumn ratio of THF to water of about 95:5.

In some embodiments, provided herein is a cocrystal comprising pomalidomide and zinc chloride with a molar ratio of pomalidomide to zinc chloride of approximately 2:1 to 1:2. In some embodiments, the molar ratio of pomalidomide to zinc chloride is approximately 1:1.

A representative XRPD pattern of a solid form comprising pomalidomide and zinc chloride is provided in FIG. 12. In some embodiments, provided herein is a solid form comprising pomalidomide and zinc chloride characterized by one or more XRPD peaks (e.g., 1, 2, 3, 4, 5, 6, 7, 8, 9, 10, 11, 12, 13, 14, 15, or more peaks) selected from peaks located at the following or approximately the following positions: 2.38, 2.93, 3.22, 11.95, 12.77, 13.97, 16.61, 17.17, 18.37, 23.03, 24.00, 24.30, 24.79, 25.71, 27.90, 28.56, and 29.53 degrees 2θ, plus or minus 0.10. In some embodiments, provided herein is a solid form comprising pomalidomide and zinc chloride characterized by one or more XRPD peaks (e.g., 1, 2, 3, 4, 5, 6, 7, 8, 9, 10, 11, 12, 13, 14, 15, or more peaks) selected from peaks located at the following or approximately the following positions: 2.38, 2.93, 3.22, 11.95, 13.97, 16.61, 17.17, 18.37, 23.03, 24.00, 24.30, 24.79, 25.71, 27.90, and 28.56 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising pomalidomide and zinc chloride having an XRPD pattern comprising peaks at approximately 2.38, 17.17, and 25.71 degrees 2θ. In certain embodiments, the solid form further comprises peaks at approximately 3.22 and 16.61 degrees 2θ. In certain embodiments, the solid form further comprises peaks at approximately 11.95 and 28.56 degrees 2θ. In one embodiment, the solid form comprises peaks at approximately 2.38, 2.93, 3.22, 11.95, 13.97, 16.61, 17.17, 18.37, 23.03, 24.00, 24.30, 24.79, 25.71, 27.90, and 28.56 degrees 2θ.

In some embodiments, provided herein is a solid form comprising pomalidomide and zinc chloride having an XRPD pattern comprising peaks at approximately 2.38, 3.22, and 25.71 degrees 2θ. In some embodiments, provided herein is a solid form comprising pomalidomide and zinc chloride having an XRPD pattern comprising peaks at approximately 2.38, 11.95, and 25.71 degrees 2θ. In some embodiments, provided herein is a solid form comprising pomalidomide and zinc chloride having an XRPD pattern comprising peaks at approximately 2.38, 16.61, and 25.71 degrees 2θ. In some embodiments, provided herein is a solid form comprising pomalidomide and zinc chloride having an XRPD pattern comprising peaks at approximately 2.38, 25.71, and 28.56 degrees 2θ.

In some embodiments, the XRPD peaks above (degrees 2θ peaks) are when analyzed using copper Kα radiation. In some embodiments, provided herein is a solid form comprising pomalidomide and zinc chloride, wherein the solid form is characterized by an XRPD diffraction pattern which matches the XRPD pattern presented in FIG. 12.

5.2.13 Polymorphs of Pomalidomide

Certain embodiments herein provide solid forms comprising pomalidomide. In one embodiment, provided herein is a solid form of pomalidomide that is substantially crystalline. In one embodiment, provided herein is a crystal form of pomalidomide. In one embodiment, provided herein is a solid form of pomalidomide comprising crystalline pomalidomide.

In certain embodiments, provided herein are solid forms of pomalidomide that can be designated herein as Form A. Form A of pomalidomide has been described in International Patent Application No. PCT/US2013/026662, the entirety of which is incorporated herein by reference. A representative XRPD pattern of a solid form comprising pomalidomide is provided in FIG. 13A.

In certain embodiments, provided herein are solid forms of pomalidomide that can be designated herein as Form B. In some embodiments, the solid form comprising Form B of pomalidomide is obtained by removing solvent from a solution containing pomalidomide, with or without the presence of a coformer. In some embodiments, the solid form is obtained by removing solvent from a solution containing pomalidomide on a rotary evaporator at about 65° C. In some embodiments, the solid form is obtained by removing solvent from a solution containing pomalidomide, and subsequently storing the residue at about 75% relative humidity for 1 day. In some embodiments, the solid form is obtained by removing solvent from a solution containing pomalidomide, and subsequently storing the residue at about 60° C. overnight. In some embodiments, the solvent system is a mixed solvent of THF and water. In some embodiments, the solvent system is a mixed solvent of THF and water with a volumn ratio of THF to water of about 95:5.

A representative XRPD pattern of a solid form comprising pomalidomide is provided in FIG. 13B. In some embodiments, the XRPD peaks above (degrees 2θ peaks) are when analyzed using copper Kα radiation. In some embodiments, provided herein is a solid form comprising pomalidomide, wherein the solid form is characterized by an XRPD diffraction pattern which matches the XRPD pattern presented in FIG. 13B.

A representative thermal gravimetric analysis (TGA) curve of a solid form comprising pomalidomide is provided in FIG. 14, which exhibits a weight loss of about 1.20% of the total sample weight upon heating from about 25 to about 100° C. In some embodiments, provided herein is a solid form comprising pomalidomide, wherein the solid form is characterized by a TGA thermogram which matches the TGA thermogram presented in FIG. 14.

A representative differential scanning calorimetry (DSC) thermogram of a solid form comprising pomalidomide is presented in FIG. 14. In some embodiments, provided herein is a solid form comprising pomalidomide that exhibits a thermal event, as characterized by DSC, with a peak temperature of about 316° C. and/or an onset temperature of about 315° C. In some embodiments, provided herein is a solid form comprising pomalidomide, wherein the solid form is characterized by a DSC thermogram which matches the DSC thermogram presented in FIG. 14.

In one embodiment, Form B of pomalidomide converts to Form A of pomalidomide after slurring in EtOH, 0.1 N HCl, or water for 3 days. In one embodiment, without being limited by particular theory, Form B is a metastable form of pomalidomide.

In certain embodiments, provided herein are solid form comprising (i) a cocrystal comprising (a) pomalidomide or a pharmaceutically acceptable salt, solvate, hydrate, stereoisomer, prodrug, or clathrate thereof; and (b) a coformer; and (ii) a crystal form of pomalidomide or a pharmaceutically acceptable salt, solvate, hydrate, stereoisomer, prodrug, or clathrate thereof. In one embodiment, the crystal form of pomalidomide is Form A. In another embodiment, the crystal form of pomalidomide is Form B.

In one embodiment, provided herein is a solid form comprising (i) a cocrystal comprising pomalidomide and gallic acid; and (ii) Form A of pomalidomide.

In one embodiment, provided herein is a solid form comprising (i) a cocrystal comprising pomalidomide and vanillin; and (ii) Form A of pomalidomide.

In one embodiment, provided herein is a solid form comprising (i) a cocrystal comprising pomalidomide and D-glucose; and (ii) Form A of pomalidomide.

In one embodiment, provided herein is a solid form comprising (i) a cocrystal comprising pomalidomide and propyl gallate; and (ii) Form A of pomalidomide.

In one embodiment, provided herein is a solid form comprising (i) a cocrystal comprising pomalidomide and saccharin; and (ii) Form A of pomalidomide.

In one embodiment, provided herein is a solid form comprising (i) a cocrystal comprising pomalidomide and sodium lauryl sulfate; and (ii) Form A of pomalidomide.

In one embodiment, provided herein is a solid form comprising (i) a cocrystal comprising pomalidomide and malonic acid; and (ii) Form A of pomalidomide.

In one embodiment, provided herein is a solid form comprising (i) a cocrystal comprising pomalidomide and gallic acid; and (ii) Form B of pomalidomide.

In one embodiment, provided herein is a solid form comprising (i) a cocrystal comprising pomalidomide and magnesium bromide; and (ii) Form B of pomalidomide.

In one embodiment, provided herein is a solid form comprising (i) a cocrystal comprising pomalidomide and maltol; and (ii) Form B of pomalidomide.

In one embodiment, provided herein is a solid form comprising (i) a cocrystal comprising pomalidomide and methyl paraben; and (ii) Form B of pomalidomide.

In one embodiment, provided herein is a solid form comprising (i) a cocrystal comprising pomalidomide and vanillin; and (ii) Form B of pomalidomide.

In one embodiment, provided herein is a solid form comprising (i) a cocrystal comprising pomalidomide and zinc chloride; and (ii) Form B of pomalidomide.

5.3 Methods of Treatment, Prevention and Management

Provided herein are methods of treating, preventing, and/or managing various diseases or disorders using a solid form provided herein. In certain embodiments, provided are methods of treating, managing, and preventing various diseases and disorders, which comprise administering to a patient in need of such treatment, prevention or management a therapeutically or prophylactically effective amount of a solid form provided herein. Examples of diseases and disorders are described herein.

Examples of diseases or disorders include, but are not limited to: cancer, including hematologic cancer or solid tumor, for example, multiple myeloma, leukemia, lymphoma, sarcoma, prostate cancer, or lung cancer (e.g., small cell lung cancer); scleroderma; amyloidosis; pain, for example, complex regional pain syndrome (CRPS); myelofibrosis; myeloproliferative disease, for example, MMM; myelodysplastic syndromes (MDS); diffuse systemic sclerosis; macular degeneration; a skin disease; a pulmonary disorder; an asbestos-related disorder; a parasitic disease; an immunodeficiency disorder; a CNS disorder; a CNS injury; atherosclerosis; hemoglobinopathy; anemia, for example, sickle cell anemia; an inflammatory disease; an autoimmune disease; a viral disease; a genetic disease; an allergic disease; a bacterial disease; an ocular neovascular disease; a choroidal neovascular disease; a retina neovascular disease; rubeosis; a sleep disorder; disorders associated with angiogenesis; and TNFα related disorders.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Other examples of diseases or disorders include, but are not limited to, those described in U.S. Pat. Nos. 5,712,291, 7,393,863, and 7,863,297; and U.S. Patent Application Publication Nos. 2005/0143420, 2006/0166932, 2006/0188475, 2007/0048327, 2007/0066512, 2007/0155791, 2008/0051431, 2008/0317708, 2009/0087407, 2009/0088410, 2009/0148853, 2009/0232776, 2009/0232796, 2009/0317385, 2010/0098657, 2010/0099711, and 2011/0184025; all of which are incorporated herein by reference in their entireties.

In one embodiment is provided a method of treating, preventing and/or managing a disease provided herein, comprising administering to a patient in need of such treatment, prevention and/or management a therapeutically or prophylactically effective amount of a solid form comprising pomalidomide and a coformer as described herein and a therapeutically or prophylactically effective amount of a second active agent.

Examples of second active agents include, but are not limited to, cytokines, corticosteroids, ribonucleotide reductase inhibitors, platelet inhibitors, all-trans retinoic acids, kinase inhibitors, topoisomerase inhibitors, farnesyl transferase inhibitors, antisense oligonucleotides, vaccines, anti-cancer agents, anti-fungal agents, anti-inflammatory agents, immunosuppressive or myelosuppressive agents, and conventional therapies for MPD (e.g., prednisone). Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, etoposide, and a mixture thereof. In one embodiment, specific second active agent is dexamethasone.

Certain examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The solid forms are also useful for treating cancers of the blood and bone marrow, such as multiple myeloma and acute and chronic leukemias, for example, lymphoblastic, myelogenous, lymphocytic, and myelocytic leukemias. The solid forms provided herein can be used for treating, preventing, or managing either primary or metastatic tumors.

Other cancers include, but are not limited to, advanced malignancy, amyloidosis, neuroblastoma, meningioma, hemangiopericytoma, multiple brain metastases, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma (including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment is provided a method of treating, preventing, or managing myeloproliferative disease (MPD), comprising administering to a patient in need of such treatment, prevention, or management a therapeutically or prophylactically effective amount of a solid form comprising pomalidomide and a coformer as described herein. The embodiment encompasses the treatment, prevention or management of specific sub-types of MPD such as, but not limited to, polycythemia rubra vera (PRV), primary thromobocythemia (PT), myelofibrosis with myeloid metaplasia (MMM) and agnogenic myeloid metaplasia (AMM). In one embodiment, MPD includes: polycythemia rubra vera (PRV), primary thromobocythemia (PT), and agnogenic myeloid metaplasia (AMM). In a specific embodiment, MPD excludes leukemia. In one embodiment, particular types of MPD are MMM, PRV, PT, and AMM.

In one embodiment, a solid form comprising pomalidomide and a coformer is administered to patients who are refractory to conventional treatments for myeloproliferative diseases as well as treatments using thalidomide. As used herein, the term "refractory" means the patient's response to a MPD treatment is not satisfactory by clinical standards, e.g., showing no or little improvement of symptoms or laboratory findings.

In one embodiment is provided a method of reversing, reducing, or avoiding an adverse effect associated with the administration of an active agent used to treat MPD in a patient suffering from MPD, comprising administering to a patient in need thereof a therapeutically or prophylactically effective amount of a solid form comprising pomalidomide and a coformer as described herein. Examples of active agents include, but are not limited to, the second active agents described herein (see paragraph [00190] supra).

Examples of adverse effects associated with active agents used to treat MPD include, but are not limited to: conversion to acute leukemia; severe myelosuppression; gastrointestinal toxicity such as, but not limited to, early and late-forming diarrhea and flatulence; gastrointestinal bleeding; nausea; vomiting; anorexia; leukopenia; anemia; neutropenia; asthenia; abdominal cramping; fever; pain; loss of body weight; dehydration; alopecia; dyspnea; insomnia; dizziness; mucositis; xerostomia; mucocutaneous lesions; and kidney failure.

In one embodiment, provided herein is a method of treating, preventing, or managing MPD, comprising administering to a patient (e.g., a human) a solid form comprising pomalidomide and a coformer as described herein, before, during, or after transplantation therapy.

In one embodiment, provided herein are pharmaceutical compositions, single unit dosage forms, and kits, comprising a solid form comprising pomalidomide and a coformer as described herein, a second active ingredient, and/or blood or cells for transplantation therapy. For example, a kit may comprise a solid form comprising pomalidomide and a coformer as described herein, stem cells for transplantation, an immunosuppressive agent, and an antibiotic or other drug.

In one embodiment, provided herein is a method of modulating the differentiation of $CD34^+$ stem, precursor, or progenitor cells to a predominantly erythroid lineage, comprising administering to a patient an effective amount of a solid form comprising pomalidomide and a coformer as described herein.

In one embodiment, provided herein is a method of modulating differentiation of a $CD34^+$ cell to an erythroid lineage comprising differentiating said cell under suitable conditions and in the presence of pomalidomide.

The $CD34^+$ cell may be any stem, progenitor, or committed cell able to differentiate into an erythroid cell. Such cells may be totipotent or pluripotent, or may be committed to a hematopoietic lineage. The $CD34^+$ cell may be derived from any source; in particular embodiments, "embryonic-like" stem cells derived from the placenta. For a description of such embryonic-like stem cells and methods of obtaining them, see U.S. application publication no. US 2003/0180269 A1, published Sep. 25, 2003, which is incorporated by reference herein in its entirety. Other $CD34^+$ cells useful for the methods provided herein include stem cells obtained from any tissue (such as, for example, hematopoietic stem cells or embryonic stem cells) and non-committed progenitor cells from any tissue. Such $CD34^+$ cells may be heterologous or autologous with reference to the intended recipient, when such cells, the differentiation of which is modulated according to the methods provided herein, are used to treat anemia or a hemoglobinopathy.

Differentiation of the $CD34^+$ cells may typically take place over the course of 3-6 days. In in vitro assays in which $CD34^+$ cells are cultured in the presence of pomalidomide, changes in gene expression indicating differentiation along an erythroid pathway may be evident by the third day of culture. In one embodiment, erythroid-specific gene expression is significantly increased, and phenotypic characteristics of erythroid cells are present in the $CD34^+$ cells by day 6 of culture.

In one embodiment, therefore, $CD34^+$ cells may be cultured in vitro in the presence of pomalidomide, for a period of days sufficient for erythroid-specific gene expression, particularly fetal hemoglobin gene expression, and/or cell characteristics to appear. In various embodiments, the $CD34^+$ cells may be cultured for 3, 6, 9, or 12 days, or more. A solid form comprising pomalidomide and a coformer or a solution thereof may be introduced once at the start of culture, and culturing continued until differentiation is substantially complete, or for 3, 6, 9, 12 or more days. Alternatively, a solid form comprising pomalidomide and a coformer or a solution thereof may be administered to a culture of $CD34^+$ cells a plurality of times during culture. The $CD34^+$ cells may be cultured and differentiated in the presence pomalidomide.

In one embodiment, a solid form comprising pomalidomide and a coformer may be used as a solution at any concentration from 0.01 µM to 10 mM. In certain embodiments, the concentration is between 0.01 µM and 10 µM.

In addition to differentiating CD34+ cells in vitro, such cells may be differentiated within an individual, in vivo. In one embodiment, such an individual is a mammal, for example a human. As with in vitro differentiation of CD34+ cells, CD34+ cells within an individual may be differentiated by administration of a solid form comprising pomalidomide and a coformer as described herein. Such administration may be in the form of a single dose. Alternatively, the individual may be administered a solid form comprising pomalidomide and a coformer as described herein a plurality of times. Such administration may be performed, for example, over a period of 3, 6, 9, 12, or more days.

Where differentiation of CD34+ cells is to be accomplished in vivo, differentiation may be accomplished using pomalidomide alone, or a combination with a second active agent. For example, for an individual having a hemoglobinopathy such as sickle cell anemia or a thalassemia, who has a higher than normal level of SCF and/or erythropoietin, in vivo differentiation may be accomplished by administration of a solid form comprising pomalidomide and a coformer as described herein. Conversely, where an individual suffers an anemia that is the result of, or is characterized by, a lower-than-normal level of erythropoietic cytokines (e.g., SCF or erythropoietin), such cytokines may be administered along with, or prior to, administration of a solid form comprising pomalidomide and a coformer. For example, an individual suffering from chemotherapy-induced anemia may be administered one or more cytokines (e.g., a combination of SCF, Flt-3L, and/or IL-3) for, e.g., 3-6 days, followed by administration for, e.g., 3-6 days, of the solid form comprising pomalidomide and a coformer, particularly with SCF and erythropoietin, in an amount sufficient to cause a detectable increase in fetal hemoglobin expression in CD34+ cells of said individual. Alternatively, CD34+ cells may be contacted with one or more cytokines in vitro (e.g., SCF, Flt-3L, and/or IL-3) for, e.g., 3-6 days, followed by administration of the cells to an individual, along with SCF and erythropoietin in an amount sufficient to cause a detectable increase in fetal hemoglobin expression in the CD34+ cells. Such administration may be performed a single time or multiple times, and any one or more of such administrations may be accompanied by the administration of a solid form comprising pomalidomide and a coformer, a second active agent, or a combination thereof.

In one embodiment is provided a method of inducing one or more genes associated with or essential for erythropoiesis or hematopoiesis, comprising contacting an hematopoietic stem, progenitor or precursor cell with pomalidomide in the presence of erythropoietin and stem cell factor, wherein said pomalidomide is present in a sufficient amount to cause said hematopoietic stem, progenitor or precursor cell to express one or more genes encoding fetal hemoglobin. In a specific embodiment, said hematopoietic stem, progenitor or precursor cell is a CD34+ cell. In another specific embodiment, said one or more genes associated with or essential for erythropoiesis or hematopoiesis are genes encoding Kruppel-like factor 1 erythroid; rhesus blood group-associated glycoprotein; glycophorin B; integrin alpha 2b; erythroid-associated factor; glycophorin A; Kell blood group precursor; hemoglobin α2; solute carrier 4, anion exchanger; carbonic anhydrase hemoglobin γA; hemoglobin γG; hemoglobin ε1; or any combination of the foregoing.

In some embodiments, the CD34+ cells are additionally differentiated, either in vivo or in vitro, in the presence of one or more cytokines. Cytokines useful to direct CD34+ cells along an erythroid differentiation pathway include, but are not limited to, erythropoietin (Epo), TNFα, stem cell factor (SCF), Flt-3L, and granulocyte macrophage-colony stimulating factor (GM-CSF). Epo and SCF are known to be erythropoietic cytokines. Thus, in one embodiment, CD34+ cells are differentiated in the presence of Epo or SCF. In another embodiment, the CD34+ cells are differentiated in the presence of Epo and SCF. In another embodiment, the CD34+ cells are differentiated in the presence of a combination of TNFα, SCF, Flt-3L, and/or GM-CSF. In another embodiment, said cells that are differentiated are one or more cells in cell culture. In another embodiment, said cells that are differentiated are cells within an individual. In an embodiment of in vitro differentiation, one or more of Epo, TNFα, SCF, Flt-3L and GM-CSF is contacted with pomalidomide. In an embodiment of in vivo differentiation, one or more of Epo, TNFα, SCF, Flt-3L and GM-CSF is administered to an individual in the same treatment regimen a the solid form comprising pomalidomide and a coformer as provided herein.

The cytokines used in the methods provided herein may be naturally-occurring cytokines, or may be an artificial derivative or analog of the cytokines. For example, analogs or derivatives of erythropoietin that may be used in combination with a solid form or compound provided herein include, but are not limited to, Aranesp™ and Darbopoietin™.

Cytokines used may be purified from natural sources or recombinantly produced. Examples of recombinant cytokines that may be used in the methods provided herein include filgrastim, or recombinant granulocyte-colony stimulating factor (G-CSF), which is sold in the United States under the trade name Neupogen® (Amgen, Thousand Oaks, Calif.); sargramostim, or recombinant GM-CSF, which is sold in the United States under the trade name Leukine® (Immunex, Seattle, Wash.); recombinant Epo, which is sold in the United States under the trade name Epogen® (Amgen, Thousand Oaks, Calif.); and methionyl stem cell factor (SCF), which is sold in the United States under the trade name Ancestim™. Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Other cytokines may be used which encourage the survival and/or proliferation of hematopoietic precursor cells and immunologically active poietic cells in vitro or in vivo, or which stimulate the division and differentiation of committed erythroid progenitors in cells in vitro or in vivo. Such cytokines include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF.

When administered to a person having a hemoglobinopathy, a solid form comprising pomalidomide and a coformer as described herein, particularly in the presence of Epo, particularly in the presence of the combination of TNFα, SCF, Flt-3L and GM-CSF, or more particularly in the presence of Epo and SCF, induces the production of erythrocytes, and the production of fetal hemoglobin as well as the production of AHSP. As noted above, cytokines used may include purified or recombinant forms, or analogs or derivatives of specific cytokines.

A solid form comprising pomalidomide and a coformer as described herein may also be administered in conjunction with one or more second compounds known to have, or suspected of having, a beneficial effect on a hemoglobinopathy. In this context, "beneficial effect" means any reduction of any symptom of a hemoglobinopathy or anemia.

For example, with specific reference to the hemoglobinopathy sickle cell anemia, the second compound can be a compound, other than a pomalidomide or a derivative thereof, that is known or suspected to induce the production of fetal hemoglobin. Such compounds include hydroxyurea, and butyrates or butyrate derivatives. The second compound may also be a compound that relaxes blood vessels, such as nitrous oxide, e.g., exogenously-applied or administered nitrous oxide. The second compound may also be a compound that binds directly to hemoglobin S, preventing it from assuming the sickle-inducing conformation. For example, the plant extract known as HEMOXIN™ (NIPRISAN™; see U.S. Pat. No. 5,800,819), which is an extract of a mixture of about 12 to about 17 parts by weight of *Piper guineense* seeds, from about 15 to about 19 parts by weight of *Pterocarpus osun* stem, from about 12 to about 18 parts by weight of *Eugenia caryophyllata* fruit, and from about 25 to about 32 parts by weight of *Sorghum bicolor* leaves, and optionally 15-22 parts by weight potash, wherein the mixture is extracted with cold water, has antisickling activity. The second compound may also be a Gardos channel antagonist. Examples of Gardos channel antagonists include clotrimazole and triaryl methane derivatives. The second compound may also be one that reduces red blood cell adhesion, thereby reducing the amount of clotting pervasive in sickle cell anemia.

Other hemoglobinopathies may be treated with a second compound known or suspected to be efficacious for the specific condition. For example, β thalassemia may additionally be treated with the second compound Deferoxamine, an iron chelator that helps prevent the buildup of iron in the blood, or folate (vitamin B9). Thalassemia or sickle cell anemia may also be treated with protein C as the second compound (U.S. Pat. No. 6,372,213). There is some evidence that herbal remedies can ameliorate symptoms of hemoglobinopathies, e.g., thalassemia; such remedies, and any of the specific active compounds contained therein, may also be used as a second compound in the method provided herein. See, e.g., Wu Zhikui et al. "The Effect of Bushen Shengxue Fang on β-thalassemia at the Gene Level," *Journal of Traditional Chinese Medicine* 18(4): 300-303 (1998); U.S. Pat. No. 6,538,023 "Therapeutic Uses of Green Tea Polyphenols for Sickle Cell Disease". Treatment of autoimmune hemolytic anemia can include corticosteroids as the second compound.

Second compounds that are proteins may also be derivatives or analogs of other proteins. Such derivatives may include, but are not limited to, proteins that lack carbohydrate moieties normally present in their naturally occurring forms (e.g., nonglycosylated forms), pegylated derivatives, and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Cytokines and/or other compounds potentially useful in the treatment of anemia or a hemoglobinopathy may be administered at the same time as pomalidomide or a derivative thereof. In this regard, the cytokines or other compounds may be administered as formulations separate from a solid form comprising pomalidomide and a coformer, or, where possible, may be compounded with a solid form comprising pomalidomide and a coformer for administration as a single pharmaceutical composition. Alternatively, the cytokines, the other compounds, or both, may be administered separately from a solid form comprising pomalidomide and a coformer used in the methods provided herein, and may follow the same or different dosing schedules. In one embodiment, a solid form comprising pomalidomide and a coformer, cytokines, and/or any other compound useful to treat anemia or a hemoglobinopathy, are administered at the same time, but in separate pharmaceutical formulations for flexibility in administration.

In addition to the treatment combinations outlined herein, the treated individual may be given transfusions. Such transfusions may be of blood, for example matched blood, or of a blood substitute such as Hemospan™ or Hemospan™ PS (Sangart).

In any of the treatment combinations described herein, the treated individual is eukaryotic. In one embodiment, the treated individual is a mammal, for example a human.

The methods described herein may be used to treat any anemia, including anemia resulting from a hemoglobinopathy. Hemoglobinopathies and anemias treatable by the methods provided herein may be genetic in origin, such as sickle-cell anemia or thalassemias. The hemoglobinopathy may be due to a disease, such as cancer, including, but not limited to, cancers of the hematopoietic or lymphatic systems. Other conditions treatable using the methods provided herein include hypersplenism, splenectomy, bowel resection, and bone marrow infiltration. The methods described herein may also be used to treat anemia resulting from the deliberate or accidental introduction of a poison, toxin, or drug. For example, anemias resulting from cancer chemotherapies may be treated using the methods and solid forms provided herein. As such, the methods described herein may be employed when anemia or a hemoglobinopathy is the primary condition to be treated, or is a secondary condition caused by an underlying disease or treatment regimen.

In one embodiment, the diseases or disorders are various forms of leukemias such as chronic lymphocytic leukemia, chronic myelocytic leukemia, acute lymphoblastic leukemia, acute myelogenous leukemia, and acute myeloblastic leukemia, including leukemias that are relapsed, refractory, or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia, and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, the diseases or disorders are various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver, and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Other disease or disorders treated, prevented, or managed include, but not limited to, viral, genetic, allergic, and autoimmune diseases. Specific examples include, but are not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

In certain embodiments, a solid form provided herein, or a composition comprising a solid form provided herein, is administered orally, parenterally, topically, or mucosally. Examples of such dosage forms can be found in section 5.5, infra.

In certain embodiments, a solid form provided herein, or a composition comprising a solid form provided herein, is administered at a dosing frequency of once, twice, thrice, or four times daily. In certain embodiments, solid form provided herein, or a composition comprising a solid form provided herein, comprises pomalidomide in an amount of from about 0.1 to about 100 mg, from about 0.5 to about 50 mg, from, about 0.5 to about 25 mg, from about 1 mg to about 10 mg, from about 0.5 to about 5 mg, or from about 1 mg to about 5 mg. In certain embodiments, provided herein is a single unit dosage form suitable for oral administration to a human comprising: an amount equal to or greater than about 1, 2, 3, 4, or 5 mg of a solid form comprising pomalidomide and a coformer provided herein; and a pharmaceutically acceptable excipient. In one embodiment, the amount of the active ingredient is about 0.5 mg. In another embodiment, the amount of the active ingredient is about 1 mg. In another embodiment, the amount of the active ingredient is about 2 mg. In another embodiment, the amount of the active ingredient is about 4 mg.

In one embodiment, the second active agent is administered intravenously or subcutaneously and once or twice daily, once every other day, once every week, once every two weeks, or once every three weeks, in an amount of from about 1 to about 1000 mg, from about 5 to about 500 mg, from about 10 to about 350 mg, or from about 50 to about 200 mg. In one embodiment, the second active agent is administered orally and once or twice daily, once every other day, once every week, once every two weeks, or once every three weeks, in an amount of from about 1 to about 1000 mg, from about 5 to about 500 mg, from about 10 to about 350 mg, from about 10 to about 200 mg, from about 10 to about 100 mg, or from about 20 to about 50 mg. In specific embodiments, the second active agent is administered once every week in an amount of about 40 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

5.4 Cycling Therapy

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 5 mg per day, followed by a rest of one or two weeks. In other embodiments, the dose can be from about 1 mg to about 5 mg per day (e.g., 1, 2, 3, or 4 mg/day), given on Days 1-21 of each 28-day cycle until disease progression, followed by a rest of 7 days on Days 22-28 of each 28-day cycle, for example, in patients with relapsed and refractory multiple myeloma who are refractory to their last myeloma therapy and have received at least 2 prior therapies that included lenalidomide and bortezomib.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

In one embodiment, a compound provided herein is administered at a dose of about 4 mg per day given on Days 1-21, followed by a rest of 7 days on Days 22-28 of each 28-day cycle, alone or in combination with low dose dexamethasone (e.g., 40 mg/day given on Days 1, 8, 15 and 22 of each 28-day cycle), for example, in patients with relapsed and refractory multiple myeloma who are refractory to their last myeloma therapy and have received at least 2 prior therapies that included lenalidomide and bortezomib.

5.5 Pharmaceutical Compositions and Dosage Forms

Pharmaceutical compositions can be used in the preparation of single unit dosage forms comprising one or more solid forms provided herein. In one embodiment, provided herein are pharmaceutical compositions and dosage forms comprising one or more solid forms comprising a compound provided herein, or a pharmaceutically acceptable salt, solvate (e.g., hydrate), stereoisomer, co-crystal, clathrate, or prodrug thereof. Pharmaceutical compositions and dosage forms provided herein can further comprise one or more pharmaceutically acceptable excipients or carriers.

In some embodiments, pharmaceutical compositions and dosage forms provided herein can also comprise one or more additional active ingredients. Examples of optional second, or additional, active ingredients are disclosed herein elsewhere.

In one embodiment, single unit dosage forms provided herein are suitable for oral, parenteral (e.g., subcutaneous, intravenous, bolus injection, intramuscular, or intraarterial), topical (e.g., eye drops or other ophthalmic preparations), mucosal (e.g., nasal, sublingual, vaginal, buccal, or rectal), or transdermal administration to a patient. Examples of dosage forms include, but are not limited to: tablets; caplets; capsules, such as soft elastic gelatin capsules or hard gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient. In one embodiment, the single dosage forms provided herein are tablets, caplets, or capsules comprising one or more solid forms provided herein. In one embodiment, the single dosage forms provided herein are tablets or capsules comprising one or more solid forms provided herein.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences,* 18th ed., Mack Publishing, Easton Pa. (1990).

In one embodiment, pharmaceutical compositions and dosage forms comprise one or more excipients or carriers. Suitable excipients are known to those skilled in the art of pharmacy, and non-limiting examples of suitable excipients are provided herein. Whether a particular excipient is suitable for incorporation into a pharmaceutical composition or dosage form depends on a variety of factors known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, in one embodiment, provided are pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient. Lactose-free compositions provided herein can comprise excipients which are known in the art and are listed in the *U.S. Pharmacopeia* (USP) 25-NF20 (2002), which is incorporated herein in its entirety.

Also provided are anhydrous pharmaceutical compositions and dosage forms comprising active ingredient(s), since water may facilitate the degradation of some compounds. Anhydrous pharmaceutical compositions and dosage forms can be prepared using anhydrous or low moisture containing ingredients and low moisture or low humidity conditions. An anhydrous pharmaceutical composition should be prepared and stored such that its anhydrous nature is maintained. Accordingly, in one embodiment, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise the active ingredient or solid form comprising pomalidomide and a coformer provided herein in an amount of from about 0.10 to about 10 mg, or from about 0.10 to about 5 mg. In other embodiments, dosage forms comprise a compound provided herein in an amount of about 0.1, 0.2, 0.3, 0.4, 0.5, 0.6, 0.7, 0.8, 0.9, 1, 2, 2.5, 3, 4, or 5 mg.

In other embodiments, dosage forms comprise a second active ingredient in an amount from about 1 mg to about 1000 mg, from about 5 mg to about 500 mg, from about 10 mg to about 350 mg, from about 5 mg to about 250 mg, from about 5 mg to about 100 mg, from about 10 mg to about 100 mg, from about 10 mg to about 50 mg, or from about 50 mg to about 200 mg. In one embodiment, the specific amount of the second active agent will depend on the specific agent used, the diseases or disorders being treated or managed, and the amount(s) of a compound provided herein, and any optional additional active agents concurrently administered to the patient.

In particular embodiments, provided herein is a pharmaceutical composition comprising a solid form comprising pomalidomide and a coformer provided herein and a pharmaceutically acceptable excipient or carrier. In particular embodiments, provided herein is a pharmaceutical composition comprising a cocrystal comprising pomalidomide and a coformer provided herein and a pharmaceutically acceptable excipient or carrier. In particular embodiments, provided herein is a pharmaceutical composition comprising an amorphous pomalidomide provided herein and a pharmaceutically acceptable excipient or carrier. Exemplary embodiments of formulations of pomalidomide are described in, for example, U.S. Pat. Nos. 5,635,517, 6,335,349, 6,316,471, 6,476,052, 7,041,680, and 7,709,502; and U.S. Patent Application Publication No. 2011/0045064; the entireties of which are incorporated herein by reference.

5.5.1 Oral Dosage Forms

Pharmaceutical compositions that are suitable for oral administration can be provided as discrete dosage forms, such as, but not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In one embodiment, such dosage forms contain predetermined amounts of active ingredients, and may be prepared by methods of pharmacy known to those skilled in the art. See generally, *Remington's Pharmaceutical Sciences,* 18th ed., Mack Publishing, Easton Pa. (1990). As used herein, oral administration also includes buccal, lingual, and sublingual administration.

In one embodiment, the oral dosage form provided herein is a tablet. In one embodiment, the oral dosage form provided herein is a capsule. In one embodiment, the oral dosage form provided herein is a caplet. In particular embodiments, In one embodiment, oral dosage forms provided herein are prepared by combining the active ingredients in an intimate admixture with one or more pharmaceutically acceptable carrier or excipient, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide, according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In specific embodiments, capsules comprising one or more solid forms comprising pomalidomide and a coformer provided herein can be used for oral administration. In one embodiment, the total amount of pomalidomide in the capsule is about 1 mg, about 2 mg, about 3 mg, about 4 mg, or about 5 mg. In one embodiment, the total amount of pomalidomide in the capsule is about 1 mg, about 2 mg, or about 4 mg. In one embodiment, the total amount of pomalidomide in the capsule is about 1 mg or about 2 mg. Each capsule can contain pomalidomide as the active ingredient and one or more of the following inactive ingredients: mannitol, pregelatinized starch and sodium stearyl fumarate. In specific embodiments, the 1 mg capsule shell can contain gelatin, titanium dioxide, FD&C blue 2, yellow iron oxide, white ink and black ink. In specific embodiments, the 2 mg capsule shell can contain gelatin, titanium dioxide, FD&C blue 2, yellow iron oxide, FD&C red 3 and white ink. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, the dosage form is a tablet, wherein the tablet is manufactured using standard, art-recognized tablet processing procedures and equipment. In certain embodiments, the method for forming the tablets is direct compression of a powdered, crystalline and/or granular composition comprising a solid form provided herein, alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the dosage form is a capsule, wherein the capsules may be manufactured using standard, art-recognized capsule processing procedures and equipments. In certain embodiments, soft gelatin capsules may be prepared in which the capsules contain a mixture comprising a solid form provided herein and vegetable oil or non-aqueous, water miscible materials, such as, for example, polyethylene glycol and the like. In certain embodiments, hard gelatin capsules may be prepared containing granules of solid forms provided herein in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

Examples of excipients or carriers that can be used in oral dosage forms provided herein include, but are not limited to, diluents (bulking agents), lubricants, disintegrants, fillers, stabilizers, surfactants, preservatives, coloring agents, flavoring agents, binding agents (binders), excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, dosage forms provided herein comprise one or more binders. Binders may be used, e.g., to impart cohesive qualities to a tablet or a capsule, and thus ensure that the formulation remains intact after compression. Suitable binders include, but are not limited to, starch (including potato starch, corn starch, and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone (PVP), cellulosic polymers (including hydroxypropyl cellulose (HPC), hydroxypropylmethylcellulose (HPMC), methyl cellulose, ethyl cellulose, hydroxyethyl cellulose (HEC), carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethacrylates, povidone, sodium alginate, sodium carboxymethylcellulose, starch, pregelatinized starch, stearic acid, sucrose, and zein. In one embodiment, the binding agent can be, relative to the weight of the dosage form, in an amount of from about 50% to about 99% w/w. In certain embodiments, a suitable amount of a particular binder is determined by one of ordinary skill in the art.

Suitable forms of microcrystalline cellulose include, but are not limited to, the materials sold as AVICEL-PH-101, AVICEL-PH-103 AVICEL RC-581, AVICEL-PH-105 (FMC Corporation, Marcus Hook, Pa.), and mixtures thereof. In one embodiment, a specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in a pharmaceutical composition is, in one embodiment, present in from about 50 to about 99 weight percent of the pharmaceutical composition or dosage form.

In certain embodiments, dosage forms provided herein comprise one or more diluents. Diluents may be used, e.g., to increase bulk so that a practical size tablet or capsule is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule. The amount of a diluent in the pharmaceutical compositions provided herein varies upon the type of formulation, and is readily discernible to those of ordinary skill in the art.

Disintegrants may be used in the compositions to provide tablets or capsules that disintegrate when exposed to an aqueous environment. Dosage forms that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredient(s) may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

In one embodiment, a solid oral dosage form comprises a compound provided herein, and one or more excipients selector from anhydrous lactose, microcrystalline cellulose, polyvinylpyrrolidone, stearic acid, colloidal anhydrous silica, and gelatin. In one embodiment, capsules comprise one or more solid forms comprising pomalidomide and a coformer provided herein, and one or more of the following inactive ingredients: mannitol, pregelatinized starch, sodium stearyl fumarate, gelatin, titanium dioxide, FD&C blue 2, yellow iron oxide, white ink, black ink, FD&C red 3, and a combination thereof.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

6. EXAMPLES

Certain embodiments provided herein are illustrated by the following non-limiting examples.

In one embodiment, pomalidomide may be synthesized using methods described in U.S. Pat. Nos. 5,635,517, 6,335,349, 6,316,471, 6,476,052, 7,041,680, 7,709,502, and 7,994,327, all of which are incorporated herein in their entireties.

6.1 Preparation of Cocrystal Comprising Pomalidomide and a Coformer

Method A (Stoichiometric Slurry Experiments): Stoichiometric slurry experiments were carried out in glass vials. Each of the vials was charged with about 20 mg of pomalidomide, an approximately equimolar amount of coformer, and 5000 μ, of a saturated solution of the same coformer in the solvent used for that experiment. A magnetic stir bar was placed in each vial and the rack of vials was placed on a stir plate at room temperature for 24 hours. The solids were isolated by centrifugation.

Method B (Stoichiometric Wet Milling Experiments): For each experiment, A PEEK grinding cup was charged with about 20 mg of pomalidomide, an approximately equimolar amount of coformer, about 100 μL of a mixture of methanol and water (3:1), and one steel grinding ball. The cup was sealed and shaken on a Retsch mill for 20 min. The solid was collected.

Method C (Stoichiometric Flash Evaporation Experiments): The solvent was removed from solutions containing about 20 mg of pomalidomide and approximately equimolar amount of coformer on a rotary evaporator using a bath set at 65° C. If the residue was solid it was stored at 75% relative humidity for 1 day. If the residue was oil it was stored at 60° C. overnight. The resulting solids were collected.

In one exemplary study, a cocrystal comprising pomalidomide and gallic acid was prepared by method A as described above using a solvent of DMF:acetone (1:2). In another embodiment, a cocrystal comprising pomalidomide and gallic acid was prepared by method C as described above.

In one exemplary study, a cocrystal comprising pomalidomide and vanillin was prepared by method B as described above. In another embodiment, a cocrystal comprising pomalidomide and vanillin was prepared by method C as described above.

In one exemplary study, a cocrystal comprising pomalidomide and cyclamic acid was prepared by method A as described above using a solvent of DMF:acetone (1:2).

In one exemplary study, a cocrystal comprising pomalidomide and D-glucose was prepared by method A as described above using a solvent of DMF:MeOH (1:1).

In one exemplary study, a cocrystal comprising pomalidomide and propyl gallate was prepared by method A as described above using a solvent of DMF:MeOH (1:1).

In one exemplary study, a cocrystal comprising pomalidomide and saccharin was prepared by method A as described above using a solvent of DMF:MeOH (1:1).

In one exemplary study, a cocrystal comprising pomalidomide and sodium lauryl sulfate was prepared by method B as described above.

In one exemplary study, a cocrystal comprising pomalidomide and magnesium bromide was prepared by method C as described above.

In one exemplary study, a cocrystal comprising pomalidomide and malonic acid was prepared by method C as described above.

In one exemplary study, a cocrystal comprising pomalidomide and maltol was prepared by method C as described above.

In one exemplary study, a cocrystal comprising pomalidomide and methyl paraben was prepared by method C as described above.

In one exemplary study, a cocrystal comprising pomalidomide and zinc chloride was prepared by method C as described above.

In one exemplary study, a pure Form B of pomalidomide was prepared by rotary evaporation of a solution of pomalidomide in a 95:5 mixture of tetrahydrofuran and water.

All of the samples generated were analyzed by XRPD. The Rigaku Smart-Lab X-ray diffraction system was configured for reflection Bragg-Brentano geometry using a line source X-ray beam. The x-ray source was a Cu Long Fine Focus tube that was operated at 40 kV and 44 ma. That source provided an incident beam profile at the sample that changed from a narrow line at high angles to a broad rectangle at low angles. Beam conditioning slits were used on the line X-ray source to ensure that the maximum beam size was less than 10 mm both along the line and normal to the line. The Bragg-Brentano geometry was a para-focusing geometry controlled by passive divergence and receiving slits with the sample itself acting as the focusing component for the optics. The inherent resolution of Bragg-Brentano geometry was governed in part by the diffractometer radius and the width of the receiving slit used. Typically, the Rigaku Smart-Lab was operated to give peak widths of 0.1° 2θ or less. The axial divergence of the X-ray beam was controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-background holder had a small circular recess (7 mm diameter and about 1 mm depth) that held between 5 and 10 mg of powdered material. Each sample was analyzed from 2 to 40° 2θ using a continuous scan of 3° 2θ per minute with an effective step size of 0.02° 2θ.

DSC analyses were performed using a TA Instruments Q5000 DSC equipped with an autosampler tray. The instrument was cooled using a TA Instrument Refrigerated Cooling System (RCS) 90 chiller. Each sample was weighed into a Tzero DSC pan, covered with a Tzero lid, and crimped. The sample pan was placed in the DSC autosampler tray for automated loading and analysis. An empty crimped Tzero pan was used as a reference and was also placed in the autosampler tray for automated loading. During analysis, the sample was heated from ambient temperature to about 350° C. at a rate of 10° C./minute. The instrument was controlled using Thermal Advantage Release 5.2.5 software and the data were analyzed using Universal Analysis 2000 for Windows version 4.5A.

TGA analyses were performed using a TA Instruments Q50 TGA with external heat exchanger. Each sample was loaded into a platinum TGA pan, which was then loaded onto the instrument. During analysis, the sample was heated from ambient temperature to about 350° C. at a rate of 10° C./minute. The instrument was controlled using Thermal Advantage Release 5.2.5 software and the data were analyzed using Universal Analysis 2000 for Windows version 4.5A.

The general characterization methods described herein are non-limiting, and are intended merely as examples of parameters, methods and techniques which can be used to analyze certain embodiments provided herein. Other standard parameters, methods and techniques for chemical, biological, physiological and solid-state analysis are contemplated herein as means of characterizing various embodiments provided herein.

Solubility of pomalidomide in various solvents at ambient temperature was determined and is shown in Table 1. Solubility was estimated by treating a weighed sample of pomalidomide with measured aliquots of the test solvent at ambient temperature, with shaking and/or sonication between aliquots. Dissolution was determined by visual inspection. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than" if dissolution occurred on addition of the first solvent aliquot.

TABLE 1

Solubility of Pomalidomide

| Solvent | Solubility (mg/mL) |
| --- | --- |
| Acetone | 0.9 |
| Acetonitrile | <1 |
| Dichloromethane | <1 |
| DMF | >5 |
| Hexafluoroisopropanol | 2.3 |
| Methanol | <1 |
| 2-methyltetrahydrofuran | <1 |
| tetrahydrofuran (THF) | 1.1 |
| 2,2,2-trifluoroethanol | <1 |
| acetone:water (95:5) | <1 |
| DMF:acetone (1:2) | 6.0 |
| DMF:methanol (1:1) | 4.2 |

TABLE 1-continued

Solubility of Pomalidomide

| Solvent | Solubility (mg/mL) |
| --- | --- |
| DMF:methanol (1:2) | 2.4 |
| THF:water (95:5) | 3.5 |

6.2 Assays 6.2.1 TNFα Inhibition Assay in PBMC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 μg/ml streptomycin (Life Technologies).

PBMC ($2 \times 10^5$ cells) are plated in 96-well flat-bottom Costar tissue culture plates (Corning, N.Y., USA) in triplicate. Cells are stimulated with LPS (from *Salmonella abortus* equi, Sigma cat. no. L-1887, St. Louis, Mo., USA) at 1 ng/mL final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

6.2.2 IL-2 and MIP-3α Production by T Cells

PBMC are depleted of adherent monocytes by placing $1 \times 10^8$ PBMC in 10 ml complete medium (RPMI 1640 supplemented with 10% heat-inactivated fetal bovine serum, 2 mM L-glutamine, 100 U/ml penicillin, and 100 μg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1 \times 10^8$ non-adherent PBMC: 0.3 ml Sheep anti-mouse IgG beads, 15 μl anti-CD16, 15 μl anti-CD33, 15 μl anti-CD56, 0.23 ml anti-CD19 beads, 0.23 ml anti-HLA class II beads, and 56 μl anti-CD14 beads. The cells and bead/antibody mixture is rotated end-over-end for 30-60 minutes at 4° C. Purified T cells are removed from beads using a Dynal magnet. Typical yield is about 50% T cells, 87-95% CD3' by flow cytometry.

Tissue culture 96-well flat-bottom plates are coated with anti-CD3 antibody OKT3 at 5 μg/ml in PBS, 100 μl per well, incubated at 37° C. for 3-6 hours, then washed four times with complete medium 100 μl/well just before T cells are added. Compounds are diluted to 20 times of final in a round bottom tissue culture 96-well plate. Final concentrations are about 10 μM to about 0.00064 μM. A 10 mM stock of compounds provided herein is diluted 1:50 in complete for the first 20× dilution of 200 μM in 2% DMSO and serially diluted 1:5 into 2% DMSO. Compound is added at 10 μl per 200 μl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

6.2.3 Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 μM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 μl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

6.2.4 Immunoprecipitation and Immunoblot

Namalwa cells are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

6.2.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

6.2.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

6.2.7 Luciferase Assay

Namalwa cells are transfected with 4 μg of AP1-luciferase (Stratagene) per 1×10$^6$ cells and 3 μl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein in their entireties. Citation or identification of any reference in this application is not an admission that such reference is available as prior art. The full scope of the disclosure is better understood with reference to the appended claims.

What is claimed is:

1. A method of treating relapsed and refractory multiple myeloma, the method comprising administering to a patient dexamethasone in combination with a solid form comprising (a) 4-amino-2-(2,6-dioxopiperidine-3-yl)isoindoline-1,3-dione (pomalidomide); and (b) a coformer; wherein:
   the coformer is gallic acid and the solid form has an X-ray powder diffraction (XRPD) pattern comprising peaks at 15.52, 26.16, and 26.90 degrees 2θ±0.2 degrees 2θ;
   the coformer is vanillin and the solid form has an XRPD pattern comprising peaks at 13.09, 12.25, and 25.61 degrees 2θ±0.2 degrees 2θ;
   the coformer is cyclamic acid and the solid form has an XRPD pattern comprising peaks at 6.42, 7.88, and 18.54 degrees 2θ±0.2 degrees 2θ;
   the coformer is D-glucose and the solid form has an XRPD pattern comprising peaks at 12.31, 20.68, and 25.52 degrees 2θ±0.2 degrees 2θ;
   the coformer is propyl gallate and the solid form has an XRPD pattern comprising peaks at 7.78, 12.29, 25.23, and 25.61 degrees 2θ±0.2 degrees 2θ;
   the coformer is saccharin and the solid form has an XRPD pattern comprising peaks at 15.98, 17.36, and 25.10 degrees 2θ±0.2 degrees 2θ;
   the coformer is sodium lauryl sulfate and the solid form has an XRPD pattern comprising peaks at 2.66, 5.30, and 7.93 degrees 2θ±0.2 degrees 2θ;
   the coformer is magnesium bromide and the solid form has an XRPD pattern comprising peaks at 17.16, 28.76, and 29.95 degrees 2θ±0.2 degrees 2θ;
   the coformer is malonic acid and the solid form has an XRPD pattern comprising peaks at 13.99, 16.63, and 25.58 degrees 2θ±0.2 degrees 2θ;
   the coformer is maltol and the solid form has an XRPD pattern comprising peaks at 11.87, 17.09, and 25.73 degrees 2θ±0.2 degrees 2θ;
   the coformer is methyl paraben and the solid form has an XRPD pattern comprising peaks at 18.73, 21.98, and 26.70 degrees 2θ±0.2 degrees 2θ; or
   the coformer is zinc chloride and the solid form has an XRPD pattern comprising peaks at 2.38, 3.22, and 25.71 degrees 2θ±0.2 degrees 2θ; and
   wherein the patient has received at least two prior therapies.

2. The method of claim 1, wherein the coformer is gallic acid and the solid form has an X-ray powder diffraction pattern comprising peaks at 15.52, 26.16, and 26.90 degrees 2θ±0.2 degrees 2θ.

3. The method of claim 2, having an X-ray powder diffraction pattern further comprising peaks at 18.42 and 23.20 degrees 2θ±0.2 degrees 2θ.

4. The method of claim 1, wherein the coformer is vanillin and the solid form has an X-ray powder diffraction pattern comprising peaks at 13.09, 12.25, and 25.61 degrees 2θ±0.2 degrees 2θ.

5. The method of claim 4, having an X-ray powder diffraction pattern further comprising peaks at 16.91, and 28.01 degrees 2θ±0.2 degrees 2θ.

6. The method of claim 1, wherein the coformer is cyclamic acid and the solid form has an X-ray powder diffraction pattern comprising peaks at 6.42, 7.88, and 18.54 degrees 2θ±0.2 degrees 2θ.

7. The method of claim 6, having an X-ray powder diffraction pattern further comprising a peak at 19.25 degrees 2θ±0.2 degrees 2θ.

8. The method of claim 1, wherein the coformer is D-glucose and the solid form has an X-ray powder diffraction pattern comprising peaks at 12.31, 20.68, and 25.52 degrees 2θ±0.2 degrees 2θ.

9. The method of claim 8, having an X-ray powder diffraction pattern further comprising peaks at 14.08, and 17.35 degrees 2θ±0.2 degrees 2θ.

10. The method of claim 1, wherein the coformer is propyl gallate and the solid form has an X-ray powder diffraction pattern comprising peaks at 7.78, 12.29, 25.23, and 25.61 degrees 2θ±0.2 degrees 2θ.

11. The method of claim 10, having an X-ray powder diffraction pattern further comprising peaks at 14.08, 17.35, and 24.29 degrees 2θ±0.2 degrees 2θ.

12. The method of claim 1, wherein the coformer is saccharin and the solid form has an X-ray powder diffraction pattern comprising peaks at 15.98, 17.36, and 25.10 degrees 2θ±0.2 degrees 2θ.

13. The method of claim 12, having an X-ray powder diffraction pattern further comprising peaks at 20.07 and 25.73 degrees 2θ±0.2 degrees 2θ.

14. The method of claim 1, wherein the coformer is sodium lauryl sulfate and the solid form has an X-ray powder diffraction pattern comprising peaks at 2.66, 5.30, and 7.93 degrees 2θ±0.2 degrees 2θ.

15. The method of claim 14, having an X-ray powder diffraction pattern further comprising peaks at 12.20, 17.27, and 25.53 degrees 2θ±0.2 degrees 2θ.

16. The method of claim 1, wherein the coformer is magnesium bromide and the solid form has an X-ray powder diffraction pattern comprising peaks at 17.16, 28.76, and 29.95 degrees 2θ±0.2 degrees 2θ.

17. The method of claim 16, having an X-ray powder diffraction pattern further comprising peaks at 25.72 and 29.87 degrees 2θ±0.2 degrees 2θ.

18. The method of claim 1, wherein the coformer is malonic acid and the solid form has an X-ray powder diffraction pattern comprising peaks at 13.99, 16.63, and 25.58 degrees 2θ±0.2 degrees 2θ.

19. The method of claim 18, having an X-ray powder diffraction pattern further comprising peaks at 17.27 and 24.29 degrees 2θ±0.2 degrees 2θ.

20. The method of claim 1, wherein the coformer is maltol and the solid form has an X-ray powder diffraction pattern comprising peaks at 11.87, 17.09, and 25.73 degrees 2θ±0.2 degrees 2θ.

21. The method of claim 20, having an X-ray powder diffraction pattern further comprising peaks at 13.93, 14.54, and 24.25 degrees 2θ±0.2 degrees 2θ.

22. The method of claim 1, wherein the coformer is methyl paraben and the solid form has an X-ray powder diffraction pattern comprising peaks at 18.73, 21.98, and 26.70 degrees 2θ±0.2 degrees 2θ.

23. The method of claim 22, having an X-ray powder diffraction pattern further comprising peaks at 17.10, 24.38, and 29.01 degrees 2θ±0.2 degrees 2θ.

24. The method of claim 1, wherein the coformer is zinc chloride and the solid form has an X-ray powder diffraction pattern comprising peaks at 2.38, 3.22, and 25.71 degrees 2θ±0.2 degrees 2θ.

25. The method of claim 24, having an X-ray powder diffraction pattern further comprising peaks at 11.95 and 16.61 degrees 2θ±0.2 degrees 2θ.

26. The method of claim 1, wherein the molar ratio of 4-amino-2-(2,6-dioxopiperidine-3-yl)isoindoline-1,3-dione to the coformer is about 1:1.

27. The method of claim 1, wherein the prior therapies include lenalidomide and bortezomib.

* * * * *